(12) United States Patent
Skudas

(10) Patent No.: US 9,149,738 B2
(45) Date of Patent: Oct. 6, 2015

(54) CHROMATOGRAPHY METHOD

(71) Applicant: Merck Patent GmbH, Darmstadt (DE)

(72) Inventor: Romas Skudas, Mainz (DE)

(73) Assignee: Merck Patent GmbH, Darmstadt (DE)

( * ) Notice: Subject to any disclaimer, the term of this patent is extended or adjusted under 35 U.S.C. 154(b) by 169 days.

(21) Appl. No.: 13/866,060

(22) Filed: Apr. 19, 2013

(65) Prior Publication Data

US 2013/0280788 A1 Oct. 24, 2013

Related U.S. Application Data

(60) Provisional application No. 61/666,453, filed on Jun. 29, 2012.

(30) Foreign Application Priority Data

Apr. 23, 2012 (EP) ................................ 12002828

(51) Int. Cl.
*B01D 15/38* (2006.01)
*B01D 15/18* (2006.01)
*G01N 30/46* (2006.01)
*G01N 30/44* (2006.01)

(52) U.S. Cl.
CPC ........ *B01D 15/3804* (2013.01); *B01D 15/1821* (2013.01); *B01D 15/1871* (2013.01); *G01N 30/461* (2013.01); *G01N 30/468* (2013.01); *G01N 30/44* (2013.01)

(58) Field of Classification Search
CPC ........... B01D 15/3804; B01D 15/1821; B01D 15/1871
See application file for complete search history.

(56) References Cited

U.S. PATENT DOCUMENTS

| 6,409,922 B1 | 6/2002 | Kaneko et al. |
| 7,618,539 B2 | 11/2009 | Dapremont |
| 2002/0127739 A1* | 9/2002 | Pieper et al. ................... 436/515 |
| 2008/0312425 A1* | 12/2008 | Bonnerjea et al. ............ 530/413 |
| 2009/0209736 A1 | 8/2009 | Theoleyre et al. |
| 2009/0242486 A1 | 10/2009 | Dapremont |
| 2011/0091727 A1 | 4/2011 | Joehnck et al. |

FOREIGN PATENT DOCUMENTS

| CN | 101948399 A | 1/2011 |
| EP | 2108423 A1 | 10/2009 |
| WO | 2007014591 A1 | 2/2007 |

OTHER PUBLICATIONS

GE Healthcare Life Sciences, Data file 11-0025-76 AG May 2012, Ion exchange chromatography, "Capto S, Capto Q, and Capto DEAE", GE Healthcare Bio-Sciences AB, Sweden, copyright 2005-2012.*
English Translation Abstract of CN101948399A dated Jan. 19, 2011.
M. Thommes et al. "Textural characterization of native and n-alkybonded silica monoliths by mercury intrusion/extrusion, inverse size exclusion chromatography and nitrogen adsorption" Journal of Chromatography A, 1191 [2008] pp. 57-66.

(Continued)

*Primary Examiner* — Louise W Humphrey
(74) *Attorney, Agent, or Firm* — Millen, White, Zelano & Branigan, P.C.

(57) ABSTRACT

The present invention is directed to a continuous affinity chromatography method and to an apparatus to be used in such method. The method allows the use of high operational velocity while maintaining high binding capacities.

14 Claims, 29 Drawing Sheets

(56) References Cited

OTHER PUBLICATIONS

Ekta Mahajan et al. "Improving affinity chromatography resin efficiency using semi-continuous chromatography" Journal of Chromatography A, 1227 [2012] pp. 154-162.

Chandra Mohan "Buffers—A guide for the preparation and use of buffers in biological systems" Calbiochem [2003] 37 pages.

Klaus K. Unger et al. "Particle packed columns and monolithic columns in high-performance liquid chromatography-comparison and critical appraisal" ScienceDirect, Journal of Chromatography A., 1184 [2008] pp. 393-415.

T. Muller-Spath et al. "Two Step Capture and Purification of IgG2 Using Multicolumn Countercurrent Solvent Gradient Purification (MCSGP)" BioTechnology BioEngineering,vol. 107, No. 6, [2010] pp. 974-984.

\* cited by examiner

CHROMATOGRAPHY METHOD

This application claims the benefit of priority to European Patent Application No. 12002828.7, filed on Apr. 23, 2012, and U.S. Provisional Application No. 61/666,453, filed on Jun. 29, 2012. Each of above applications is incorporated herein by reference in its entirety.

The present invention is directed to a continuous chromatography method and to an apparatus to be used in such method. The method allows the use of high operational velocity while maintaining high binding capacities.

BACKGROUND OF THE INVENTION

The purification of biopharmaceutical molecules involves using chromatographic separation methods as one of wide established technologies. The usual application involves capture and polishing of the target molecule. Various chromatographic methods and resins can be applied to fulfill these tasks (e.g. normal phase, reversed phase, size exclusion and ion exchange chromatography modes). In special areas this has developed to more specific and more efficient separation methods such as affinity chromatography. The current state of art of the antibody purification is the use of ProtA modified affinity chromatography support materials to bind and separate the target molecule from the greater part of most abundant impurities (host cell proteins, host cell DNA, sugars, amino acids, growth factors and etc.). More than 30 chromatographic resins with various properties are available today in the market, providing an opportunity for the customer to find the one best suited to his application. The main differences in those products are physical (support material, particle size, particle shape and pore size) as well as chemical properties (ProtA ligand, ligand density, support matrix type) which influence the binding capacity, mass transfer properties, compressibility and robustness.

The binding capacity strongly depends on the affinity ligand, its density on the surface and its accessibility. Due to the improvements in the modification technologies, high binding capacities >30 g/L can be reached at residence times of >3 min independently from the support matrix chemistry.

On the other hand, mass transfer properties are quite variable, causing radical differences in the application. Film mass transfer and pore diffusion are two main parameters, which influence the target molecule diffusivity towards the adsorption sites. Film mass transfer is mainly influenced by the particle size and shape. The smaller the particle and the interparticle volume the greater the mass transfer and the flow resistance. Therefore, for the analytical scale applications smaller particle size is used to assure a fast mass transfer and high efficiency. But due to the pressure resistance issues, the industrial scale operations are performed at <3 bar operation pressures. Bigger particles (60 μm-120 μm) are usually chosen.

Due to the above mentioned issues, the pore diffusion is one of the most influential properties defining the mass transfer. It was shown that some materials exhibit wide pores (50-500 nm) to enable a fast mass transfer. But these materials show low binding capacities (~20 g/L), due to the low surface area. To enhance binding capacity, higher surface area is required, usually achieved through smaller pore size. Materials exhibiting ~100 nm pore sizes have shown 40 g/L (PROSEP®-vA High Capacity (Millipore Bioprocessing, Consett, UK) binding capacities, even more ~70 nm pore size exhibiting materials have shown 56 g/L (PROSEP®-vA Ultra (Millipore Bioprocessing, Consett, UK) binding capacities. Support materials with wide pore size distribution in the comparable range have shown also similar binding capacities (MABSELECT SURE® (GE Healthcare, Uppsala, Sweden). Due to the smaller pore size, the diffusion of the target molecule is slower, requiring certain target molecule residence time to achieve binding capacities above 40 g/l. The usual range of used residence times is in the range 3-6 minutes to assure that the target molecule diffuses towards the binding sites. This is important in the chromatographic process loading phase, where the support material is treated with a solution containing target molecule. The rest of the necessary affinity chromatography method steps (such as wash, elution, Strip, cleaning in place, reequilibration, etc.) can be performed faster to assure a shorter processing time. The operational velocity in this case is influenced by the support material rigidity.

Nevertheless, after the application of this specific, very selective method for about 20 years, there is an increasing need for further method optimization in pursuit of higher economic efficiency and productivity (g (target molecule)/ml (stationary phase)/h (operation time). The current status is to use big columns for higher throughput in the expense of higher investment for the higher resin amounts. Sometimes columns of 1.2 meter diameter and 10-20 cm bed height are used for mAb purification. It was recognized that there is an alternative technology that might enable economic processing, namely continuous chromatography. The basics of this method is higher resin utilization while loading to 80% of resin binding capacity instead of 60% as in standard batch without product loss, shorter operation times through splitting the sequential batch process into the parallel operation on numerous columns and therefore enabling the usage of smaller columns.

In continuous chromatography, several identical columns are connected in an arrangement that allows columns to be operated in series and/or in parallel, depending on the method requirements. Thus, all columns can be run in principle simultaneously, but slightly shifted in method steps. The procedure can be repeated, so that each column is loaded, eluted, and regenerated several times in the process. Compared to "conventional" chromatography, wherein a single chromatography cycle is based on several consecutive steps, such as loading, wash, elution and regeneration, in continuous chromatography based on multiple identical columns all these steps occur simultaneously but on different columns each. Continuous chromatography operation results in a better utilization of chromatography resin, reduced processing time and reduced buffer requirements, all of which benefits process economy. One example of continuous chromatography is simulated moving bed (SMB) chromatography. In the current years this simulated moving bed (SMB) technology was introduced to the biopharmaceutical market as well, especially to the purification of antibodies. If previously in normal batch chromatography the loading of the chromatographic column was stopped at a specific percentage of target molecule breakthrough, so now the loading can be continued in order to increase the binding capacity without target molecule losses, since a brake through fraction is loaded on the column that is following the first one.

Nevertheless, for a better economic efficiency the processing time is of the major importance since it directly influences productivity. The increase in the binding capacity is already increasing the productivity by the level on how much more material can be bound to the surface (~20-40%), but decreasing the residence time required for the target molecule to be bound on the modified surface would enhance the economic efficiency even more. Presumably, decreasing the residence time to 0.3 min will lead to 10 times increased productivity if compared to 3 min residence time. Unfortunately, decreasing the residence time during the target molecule adsorption phase leads to the decrease in the dynamic binding capacity since the rate of the mass transfer is decreased. Consequently, column loading is typically performed with velocities going up to about 600 cm/h as disclosed in US 20090209736. But as it is also actually stated in E. Mahajan et el., Journal of Chromatography A, 1227 (2012) 154-162, at higher flow rates the column binding capacity is reduced so that high flow rates are not feasible for column loading.

Surprisingly we found that an appropriate support material physical property (particle size, pore size) selection coupled with a certain continuous chromatography method enables loading velocities above 800 cm/h and more.

BRIEF DESCRIPTION OF THE INVENTION

More than 60% total binding capacities of affinity resins without or with low <5% target molecule losses during loading can be achieved using more than 800 and even more than 1000 cm/h velocities by efficiently transferring the leached target molecule from a first capture affinity column onto a second capture affinity column during the load. Simultaneously at least a third column is used for the other chromatographic process steps to enable a parallel unit operation. This results in >20% binding capacity increase if compared directly (the same unit operation conditions) to batch unit operation and >3 times decrease in operation time (usual batch unit operation is performed at 300 cm/h). This does not only work for affinity chromatography applications but also for ion exchange chromatography applications.

The present invention is consequently directed to a method of purifying target molecules from one or more impurities in a sample, the method comprising the steps of
a) providing at least three separation units having the same chromatography matrix which are at least connected so that liquid can flow from one separation unit to the subsequent one and from the last to the first separation unit
b) feeding the sample on a first separation unit so that while the sample is loaded on this separation unit wherein the sample is at a first pH and conductivity enabling the target molecules to be bound to this separation unit, said separation unit is at least part of the loading time in fluid communication with the next separation unit so that target molecules not bound to said first separation unit can bind to the next separation unit, at the same time at least washing, eluting and/or reequilibrating one separation unit different from the separation unit that is being loaded and from the one that is in fluid communication with the separation unit that is being loaded
c) switching the feed to the next separation unit
d) feeding the sample on the said next separation unit so that while the sample is being loaded on said next separation unit wherein the sample is at a first pH and conductivity enabling the target molecules to be bound to said next separation unit, said next separation unit is at least part of the loading time in fluid communication with the separation unit after the next so that target molecules not bound to said next separation unit can bind to the separation unit after the next, at the same time at least washing, eluting and/or reequilibrating one separation unit different from the separation unit that is being loaded and from the one that is in fluid communication with the separation unit that is being loaded
e) repeating steps c) and d) one or more times,
characterized in that the feed flow never stops and has a velocity above 800 cm/h and that the chromatography matrix of the separation units comprises particles with an average diameter between 30 and 200 µm and with average pore diameters in the range between 40 nm and 300 nm.

In a preferred embodiment, the feed has a velocity above 1000 cm/h.

In a preferred embodiment, three, four or five separation units having the same chromatography matrix are provided in step a). In a very preferred embodiment, only three separation units having the same chromatography matrix are provided in step a).

In a preferred embodiment, the chromatography matrix is an affinity chromatography matrix.

In another preferred embodiment, the chromatography matrix of the separation units comprises particles with average particle size diameter (d50) between 40 and 120 µm. More preferably between 55 and 100 µm.

In another preferred embodiment, the chromatography matrix of the separation units comprises particles with average pore diameters in the range between 40 nm and 300 nm. More preferably the pores of the particles that are present in the separation units have pores with average pore diameters in the range between 50 and 150 nm. More preferred, the pores of the particles have average pore diameters in the range between 60 nm and 100 nm.

In a preferred embodiment, in steps b), c) and d), the separation unit that is being loaded is not only part of the loading time but over the whole loading time in fluid communication with the next separation unit in the circle.

In another preferred embodiment in steps b), c) and d), the fluid communication between the separation unit that is being loaded and the next separation unit in the circle starts in the second half of the loading time.

In another embodiment, when washing the loaded separation unit, the wash liquid eluting from said loaded separation unit is directed to the inlet of another separation unit.

In another embodiment, when washing the loaded separation unit, the wash liquid eluting from said loaded separation unit is directed to the feedstock.

In a preferred embodiment, the sample is a clarified sample. A clarified sample is a sample that has been subjected to clarification before.

In another preferred embodiment, the purified target molecules that are elutes from the separation units and thus result from the method according to the present invention are further subjected to at least one flow through purification step.

The invention is also directed to an apparatus comprising
at least three separation units having the same chromatography matrix which are connected with connecting lines so that liquid can flow from one separation unit to the subsequent one and from the last to the first separation unit and wherein each connecting line between two separation units comprises at least one on/off valve
a solvent delivery system that is in fluid connection with the inlet of each separation unit via a branch in the connecting line between the separation units close to the inlet of each separation unit
a fluid outlet line branching from each connecting line between the separation units close to the outlet of a separation unit comprising a line with at least two branches, each branch having an on/of valve.

The present invention is also directed to a process for purifying target molecules, typically a biopharmaceutical production process, comprising the method according to the present invention. A biopharmaceutical production process is a process in which a target molecule produced in cell culture in a bioreactor is purified such that it can be used in pharmaceutical applications.

In a preferred embodiment, the process additionally comprises one or more of the following steps:
- clarification (like centrifugation and/or filtration and/or settling)
- virus inactivation
- at least one flow-through purification step, also called flow through polishing
- sterile filtration In a preferred embodiment at least two steps of the process overlap in at least a portion of their duration.

BRIEF DESCRIPTION OF THE DRAWINGS

FIG. 7a schematically shows alternative flow path for a wash of weakly or unbound target molecules elucidating the transfer of said molecules to the other separation unit. Whereas

DEFINITIONS

Figure 1:
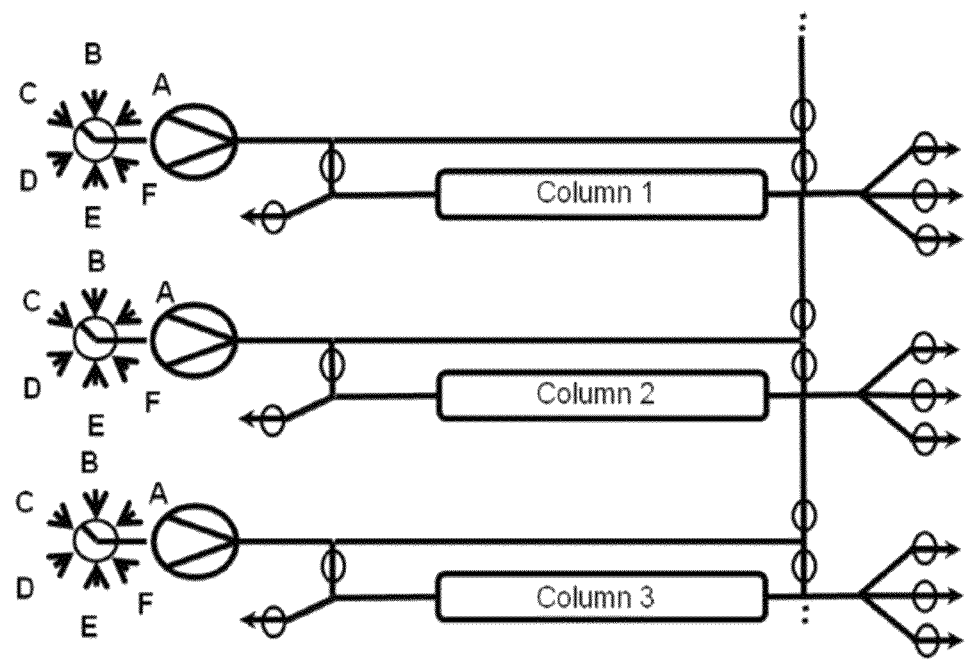
FIG. 1 shows a schematic view of a preferred embodiment of the apparatus according to the present invention. It shows the three capture separation units (ProtA, or IEX), the connections to solvent reservoirs A, B, C, D, E, F as well as the connecting lines, valves and pumps.

Before describing the present invention in detail, it is to be understood that this invention is not limited to specific compositions or process steps, as such may vary. It must be noted that, as used in this specification and the appended claims, the singular form "a", "an" and "the" include plural referents unless the context clearly dictates otherwise. Thus, for example, reference to "a ligand" includes a plurality of ligands and reference to "an antibody" includes a plurality of antibodies and the like.

Unless defined otherwise, all technical and scientific terms used herein have the same meaning as commonly understood by one of ordinary skill in the art to which this invention is related. The following terms are defined for purposes of the invention as described herein.

As used herein the term "target molecule" or "target compound" refers to any molecule, substance or compound or mixtures thereof that shall be isolated, separated or purified from one or more impurities in a sample. In a preferred embodiment, the target molecule is a protein or a mixture of two or more proteins. In a very preferred embodiment, the target molecule is an antibody. Alternatively a "target molecule" or "target compound" could be an undesired compound that shall be removed from one or more desired compounds.

The term "antibody" refers to a protein which has the ability to specifically bind to an antigen. Typically, antibodies are having a basic four-polypeptide chain structure consisting of two heavy and two light chains, said chains being stabilized, for example, by interchain disulfide bonds. Antibodies may be monoclonal or polyclonal and may exist in monomeric or polymeric form, for example, IgM antibodies which exist in pentameric form and/or IgA antibodies which exist in monomeric, dimeric or multimeric form. Antibodies may also include multispecific antibodies (e.g., bispecific antibodies), and antibody fragments so long as they retain, or are modified to comprise, a ligand-specific binding domain. The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. When produced recombinantly, fragments may be expressed alone or as part of a larger protein called a fusion protein. Exemplary fragments include Fab, Fab', F(ab')2, Fc and/or Fv fragments. Exemplary fusion proteins include Fc fusion proteins. According to the present invention fusion proteins are also encompassed by the term "antibody".

As discussed above, in some embodiments, an antibody is an Fc region containing protein, e.g., an immunoglobulin. In some embodiments, an Fc region containing protein is a recombinant protein which includes the Fc region of an immunoglobulin fused to another polypeptide or a fragment thereof. Exemplary polypeptides include, e.g., renin; a growth hormone, including human growth hormone and bovine growth hormone; growth hormone releasing factor; parathyroid hormone; thyroid stimulating hormone; lipoproteins; α-1-antitrypsin; insulin α-chain; insulin β-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-α and -β; enkephalinase; RANTES (regulated on activation normally T-cell expressed and secreted); human macrophage inflammatory protein (MIP-1-α); a serum albumin such as human serum albumin; Muellerian-inhibiting substance; relaxin α-chain; relaxin β-chain; prorelaxin; mouse gonadotropin-associated peptide; a microbial protein, such as β-lactamase; DNase; IgE; a cytotoxic T-lymphocyte associated antigen (CTLA) (e.g., CTLA-4); inhibin; activin; vascular endothelial growth factor (VEGF); receptors for hormones or growth factors; Protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β.; platelet-derived growth factor (PDGF); fibroblast growth factor such as αFGF and βFGF; epidermal growth factor (EGF); transforming growth factor (TGF) such as TGF-alpha and TGF-β, including TGF-β1, TGF-β2, TGF-β3, TGF-β4, or TGF-β5; insulin-like growth factor-I and -II (IGF-I and IGF-II); des(I-3)-IGF-I (brain IGF-I), insulin-like growth factor binding proteins (IGFBPs); CD proteins such as CD3, CD4, CD8, CD 19 CD20, CD34, and CD40; erythropoietin; osteoinductive factors; immunotoxins; a bone morphogenetic protein (BMP); an interferon such as interferon-α, -β, and -γ; colony stimulating factors (CSFs), e.g., M-CSF, GM-CSF, and G-CSF; interleukins (Ls), e.g., IL-I to IL-IO; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CDI Ia, CDI Ib, CDI Ic, CD 18, an ICAM, VLA-4 and VCAM; a tumor associated antigen such as HER2, HER3 or HER4 receptor; and fragments and/or variants of any of the above-listed polypeptides. In addition, an antibody according to the present invention is any protein or polypeptide, fragment or variant thereof, that binds specifically to any of the above-listed polypeptides.

As used herein, and unless stated otherwise, the term "sample" refers to any composition or mixture that contains a target molecule. Samples may be derived from biological or other sources. Biological sources include eukaryotic and prokaryotic sources, such as plant and animal cells, tissues and organs. The sample may also include diluents, buffers, detergents, and contaminating species, debris and the like that are found mixed with the target molecule. The sample may be "partially purified" (i.e., having been subjected to one or more purification steps, such as filtration steps) or may be obtained directly from a host cell or organism producing the target molecule (e.g., the sample may comprise harvested cell culture fluid).

The term "impurity" or "contaminant" as used herein, refers to any foreign or objectionable molecule, including a biological macromolecule such as DNA, RNA, one or more host cell proteins, endotoxins, lipids and one or more additives which may be present in a sample containing the target molecule that is being separated from one or more of the foreign or objectionable molecules using a process of the present invention.

Additionally, such impurity may include any reagent which is used in a step which may occur prior to the method of the invention.

The terms "purifying," "separating," or "isolating," as used interchangeably herein, refer to increasing the degree of purity of a target molecule from a composition or sample comprising the target molecule and one or more impurities. Typically, the degree of purity of the target molecule is increased by removing (completely or partially) at least one impurity from the composition.

The terms "bind and elute mode" and "bind and elute process," as used interchangeably herein, refer to a product separation technique in which at least one product contained in a sample (e.g., an Fc region containing protein) binds to a chromatographic resin or media and is subsequently eluted.

As used herein, the term "reservoir" as used herein, refers to any container, tank or bag, which may be used to store any buffer to be used when performing the method of the invention or the sample or any other liquid that shall be used in the method of the invention. Additionally a "reservoir" is any container, tank or bag that is used to collect the output of a process step (e.g., an eluate from a column).

The term "chromatography" refers to any kind of technique which separates an analyte of interest (e.g. a target molecule) from other molecules present in a mixture. Usually, the target molecule is separated from other molecules as a result of differences in rates at which the individual molecules of the mixture migrate through a stationary medium under the influence of a moving phase, or in bind and elute processes.

The term "matrix" or "chromatography matrix" are used interchangeably herein and refer to any kind of particulate sorbent, resin or solid phase which in a separation process separates a target molecule (e.g., an Fc region containing protein such as an immunoglobulin) from other molecules present in a mixture. Usually, the target molecule is separated from other molecules as a result of differences in rates at which the individual molecules of the mixture migrate through the matrix under the influence of a moving phase, or in bind and elute processes. The matrix consisting of resin particles can be put in columns or cartridges. Examples of materials for forming the matrix include polysaccharides (such as agarose and cellulose); and other mechanically stable matrices such as silica (e.g. controlled pore glass), poly(styrenedivinyl)benzene, polyacrylamide, ceramic particles and derivatives of any of the above. Typically the matrix carries one ore more types of ligands.

A "ligand" is a functional group that is attached to the chromatography matrix and that determines the binding properties of the matrix. Examples of "ligands" include, but are not limited to, ion exchange groups, hydrophobic interaction groups, hydrophilic interaction groups, thiophilic interactions groups, metal affinity groups, affinity groups, bioaffinity groups, and mixed mode groups (combinations of the aforementioned). Some preferred ligands that can be used herein include, but are not limited to, strong cation exchange groups, such as sulphopropyl, sulfonic acid; strong anion exchange groups, such as trimethylammonium chloride; weak cation exchange groups, such as carboxylic acid; weak anion exchange groups, such as N5N diethylamino or DEAE; hydrophobic interaction groups, such as phenyl, butyl, propyl, hexyl; and affinity groups, such as Protein A, Protein G, and Protein L.

The term "affinity chromatography" refers to a protein separation technique in which a target protein (e.g., an Fc region containing protein of interest or antibody) is specifically bound to a ligand which is specific for the target protein. Such a ligand is generally referred to as a biospecific ligand. In some embodiments, the biospecific ligand (e.g., Protein A or a functional variant thereof) is covalently attached to a chromatography matrix material and is accessible to the target protein in solution as the solution contacts the chromatography matrix. The target protein generally retains its specific binding affinity for the biospecific ligand during the chromatographic steps, while other solutes and/or proteins in the mixture do not bind appreciably or specifically to the ligand. Binding of the target protein to the immobilized ligand allows contaminating proteins or protein impurities to be passed through the chromatography matrix while the target protein remains specifically bound to the immobilized ligand on the solid phase material. The specifically bound target protein is then removed in active form from the immobilized ligand under suitable conditions (e.g., low pH, high pH, high salt, competing ligand etc.), and passed through the chromatographic column with the elution buffer, free of the contaminating proteins or protein impurities that were earlier allowed to pass through the column. Any component can be used as a ligand for purifying its respective specific binding protein, e.g. antibody. However, in various methods according to the present invention, Protein A is used as a ligand for an Fc region containing target protein. The conditions for elution from the biospecific ligand (e.g., Protein A) of the target protein (e.g., an Fc region containing protein) can be readily determined by one of ordinary skill in the art. In some embodiments, Protein G or Protein L or a functional variant thereof may be used as a biospecific ligand. In some embodiments, a biospecific ligand such as Protein A is used at a pH range of 5-9 for binding to an Fc region containing protein, washing or re-equilibrating the biospecific ligand/target protein conjugate, followed by elution with a buffer having pH about or below 4 which contains at least one salt.

The term "ion-exchange" and "ion-exchange chromatography" refers to the chromatographic process in which a solute or analyte of interest (e.g., an Fc region containing target protein) in a mixture interacts with a charged compound linked (such as by covalent attachment) to a solid phase ion exchange material such that the solute or analyte of interest interacts non-specifically with the charged compound more or less than solute impurities or contaminants in the mixture. The contaminating solutes in the mixture elute from a column of the ion exchange material faster or slower than the solute of interest or are bound to or excluded from the resin relative to the solute of interest. "Ion-exchange chromatography" specifically includes cation exchange, anion exchange, and mixed mode ion exchange chromatography. For example, cation exchange chromatography can bind the target molecule (e.g., an Fc region containing target protein) followed by elution (cation exchange bind and elution chromatography or "CIEX") or can predominately bind the impurities while the target molecule "flows through" the column (cation exchange flow through chromatography FT-CIEX). Anion exchange chromatography can bind the target molecule (e.g., an Fc region containing target protein) followed by elution or can predominately bind the impurities while the target molecule "flows through" the column. In some embodiments and as demonstrated in the Examples set forth herein, the anion exchange chromatography step is performed in a flow through mode.

The phrase "ion exchange matrix" refers to a chromatography matrix that is negatively charged (i.e. a cation exchange resin) or positively charged (i.e. an anion exchange resin). The charge may be provided by attaching one or more charged ligands to the matrix, e.g. by covalent linking. Alternatively, or in addition, the charge may be an inherent property of the matrix (e.g. as is the case for silica, which has an overall negative charge).

A "cation exchange matrix" refers to a chromatography matrix which is negatively charged, and which thus has free cations for exchange with cations in an aqueous solution passed over or through the solid phase. A negatively charged ligand attached to the solid phase to form the cation exchange resin may, e.g., be a carboxylate or sulfonate. Commercially available cation exchange resins include carboxy-methyl-cellulose, sulphopropyl (SP) immobilized on agarose (e.g., SP-SEPHAROSE FAST FLOW™ or SP-SEPHAROSE HIGH PERFORMANCE™, from Pharmacia) and sulphonyl immobilized on agarose (e.g. S-SEPHAROSE FAST FLOW™ from Pharmacia). Preferred is FRACTOGEL® EMD $SO_3$, FRACTOGEL® EMD SE Highcap, ESHMUNO® S and FRACTOGEL® EMD COO (Merck).

A "mixed mode ion exchange matrix" refers to a chromatography matrix which is covalently modified with cationic and/or anionic and hydrophobic moieties. A commercially available mixed mode ion exchange resin is BAKERBOND ABX™ (J. T. Baker, Phillipsburg, N.J.) containing weak cation exchange groups, a low concentration of anion exchange groups, and hydrophobic ligands attached to a silica gel solid phase support matrix. Mixed mode cation exchange materials typically have cation exchange groups and hydrophobic moieties. Suitable mixed mode cation exchange materials are CAPTO® MMC (GE Healthcare) and ESHMUNO® HCX (Merck). Mixed mode anion exchange materials typically have anion exchange groups and hydrophobic moieties. Suitable mixed mode anion exchange materials are CAPTO® Adhere (GE Healthcare).

The term "anion exchange matrix" is used herein to refer to a chromatography matrix which is positively charged, e.g. having one or more positively charged ligands, such as quaternary amino groups, attached thereto. Commercially available anion exchange resins include DEAE cellulose, QAE SEPHADEX™ and FAST Q SEPHAROSE™ (Pharmacia). Preferred materials are FRACTOGEL® EMD TMAE, FRACTOGEL® EMD TMAE highcap, ESHMUNO® Q and FRACTOGEL® EMD DEAE.

The terms "Protein A" and "Prot A" are used interchangeably herein and encompasses Protein A recovered from a native source thereof, Protein A produced synthetically (e.g., by peptide synthesis or by recombinant techniques), and variants thereof which retain the ability to bind proteins which have a $CH_2/CH_3$ region, such as an Fc region. Protein A can be purchased commercially from Repligen, Pharmacia and Fermatech. Protein A is generally immobilized on a chromatography matrix. The term "ProA" also refers to an affinity chromatography matrix or column containing chromatographic solid support matrix to which is covalently attached Protein A.

A functional derivative, fragment or variant of Protein A used in the methods according to the present invention may be characterized by a binding constant of at least $K=10^{-8}$ M, and preferably $K=10^{-9}$ M, for the Fc region of mouse IgG2a or human IgG1. An interaction compliant with such value for the binding constant is termed "high affinity binding" in the present context. Preferably, such functional derivative or variant of Protein A comprises at least part of a functional IgG binding domain of wild-type Protein A, selected from the natural domains E, D, A, B, C or engineered mutants thereof which have retained IgG binding functionality.

Also, Protein A derivatives or variants engineered to allow a single-point attachment may also be used in the affinity chromatography step in the claimed methods.

Single point attachment generally means that the protein moiety is attached via a single covalent bond to a chromatographic support material of the Protein A affinity chromatography. Such single-point attachment may also occur by use of suitably reactive residues which are placed at an exposed amino acid position, namely in a loop, close to the N- or C-terminus or elsewhere on the outer circumference of the protein fold. Suitable reactive groups are e.g. sulfhydryl or amino functions.

The term "affinity chromatography matrix" is used herein to refer to a chromatography matrix which carries ligands suitable for affinity chromatography. Typically the ligands (e.g., Protein A or a functional variant thereof) are covalently attached to a chromatography matrix material and are accessible to the target molecule in solution as the solution contacts the chromatography matrix. One example of an affinity chromatography matrix is a proteinA matrix. An affinity chromatography matrix typically binds the target molecules with high specificity based on a lock/key mechanism such as antigen/antibody or enzyme/receptor binding.

Examples of affinity matrices are matrices carrying protein A ligands like Protein A SEPHAROSE™ or PROSEP®-A.

The term "binding" as used herein to describe interactions between a target molecule (e.g., an Fc region containing protein) and a ligand attached to a matrix (e.g., Protein A bound to a solid phase matrix or resin), refers to the generally reversible binding of the target molecule to a ligand through the combined effects of spatial complementarity of e.g. protein and ligand structures at a binding site coupled with electrostatic forces, hydrogen bonding, hydrophobic forces, and/or van der Waals forces at the binding site. Generally, the greater the spatial complementarity and the stronger the other forces at the binding site, the greater will be the binding specificity of a protein for its respective ligand. Non-limiting examples of specific binding includes antibody-antigen binding, enzyme-substrate binding, enzyme-cofactor binding, metal ion chelation, DNA binding protein-DNA binding, regulatory protein-protein interactions, and the like. Ideally, in affinity chromatography specific binding occurs with an affinity of about $10^{-4}$ to $10^{-8}$ M in free solution.

The term "detergent" refers to ionic and nonionic surfactants such as polysorbates (e.g. polysorbates 20 or 80); poloxamers (e.g. poloxamer 188); Triton™; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyldimethylamine; sodium methyl cocoyl-, or disodium methyl oleyl-taurate; and the MONAQU AT™ series (Mona Industries, Inc., Paterson, N. J.), Useful detergents is a polysorbate, such as polysorbate 20 (TWEEN 20®.) or polysorbate 80 (TWEEN 80®.) or various acids, such as octanoic acid.

A "buffer" is a solution that resists changes in pH by the action of its acid-base conjugate components. Various buffers which can be employed depending, for example, on the desired pH of the buffer are described in Buffers. A Guide for the Preparation and Use of Buffers in Biological Systems, Gueffroy, D., ed. Calbiochem Corporation (1975). Non-limiting examples of buffers include MES, MOPS, MOPSO, Tris, HEPES, phosphate, acetate, citrate, succinate, and ammonium buffers, as well as combinations of these.

According to the present invention the term "buffer" or "solvent" is used for any liquid composition that is used to load, wash, elute and reequilibrate the separation units.

When "loading" a separation column a buffer is used to load the sample or composition comprising the target molecule (e.g., an Fc region containing target protein) and one or more impurities onto a chromatography column (e.g., an affinity column or an ion exchange column). The buffer has a conductivity and/or pH such that the target molecule is bound to the chromatography matrix while ideally all the impurities are not bound and flow through the column.

When "loading" a separation column to "flow through" a target molecule a buffer is used to load the sample or composition comprising the target molecule (e.g., an Fc region containing target protein) and one or more impurities onto a chromatography column (e.g., an affinity column or an ion exchange column). The buffer has a conductivity and/or pH such that the target molecule is not bound to the chromatography matrix and flow through to column while ideally all the impurities are bound the column.

The term "reequilibrating" refers to the use of a buffer to re-equilibrate the chromatography matrix prior to loading the target molecule. Typically, the loading buffer is used for reequilibrating.

By "wash" or "washing" a chromatography matrix is meant passing an appropriate liquid, e.g. a buffer through or over the matrix. Typically washing is used to remove weakly bound contaminants from the matrix prior to eluting the target molecule and/or to remove non-bound or weakly bound target molecule after loading.

In this case, typically, the wash buffer and the loading buffer are be the same. In case virus inactivation buffer is used, it is used to inactivate certain present virus prior to eluting the target molecule. In this case, typically, the virus inactivation buffer differs from loading buffer since it may contain detergent/detergents or have different properties (pH/conductivity/salts and their amounts).

To "elute" a molecule (e.g., a polypeptide of interest or an impurity) from a chromatography matrix is meant to remove the molecule therefrom by altering the solution conditions such that buffer competes with the molecule of interest for the ligand sites on the chromatography resin. A non-limiting example is to elute a molecule from an ion exchange resin by altering the ionic strength of the buffer surrounding the ion exchange material such that the buffer competes with the molecule for the charged sites on the ion exchange material.

According to the present invention a "separation unit" is an equipment onto which a chromatographic separation step can be performed. A separation unit typically is a chromatography column or chromatography cartridge which is filled with a sorbent matrix. Chromatography columns are known to a person skilled in the art. They typically comprise a column tube with end-fittings for fluid-inlet and fluid-outlet. The column tube is filled with a suitable chromatography matrix.

According to the present invention a "continuous" process is a process that is not run in the batch mode. In a continuous process according to the invention new sample is loaded onto one or more separation units continuously without any breaks in between. In a continuous process according to the present invention, the feed never stops.

According to the present invention, a "semi continuous process" is a process in which the feed is interrupted at least once, typically several times in a sequential manner.

According to the invention "sequential" is two times or more than two times.

According to the present invention a "connecting line" is any tube, hose, pipe or channel which is suitable for flowing liquids there through. A connecting line can be interrupted by one or more valves. A connecting line might be straight or branched.

According to the present invention if two parts of an apparatus are "in fluid connection" it means that there is a connecting line between the two parts of the apparatus so that liquid can flow from one part to the other. This connecting line can be direct or it can be interrupted by one or more valves, by a separation unit or other parts of the apparatus. The term "in fluid connection" encompasses a fluid connection that is permanent but it also encompasses a fluid connection that is not permanent and is made of a connecting line that is e.g. interrupted by one or more valves so that the flow of liquid through the connecting line can started and stopped whenever necessary. Typically, most of the parts of the apparatus that are in fluid connection have a fluid connection that is not permanent. For example, if a buffer reservoir is in fluid connection with a separation unit this means that a flow of the buffer to the column can be realized if necessary but typically there is at least one valve located in the connecting line between the reservoir and the separation unit so that the liquid flow can be stopped when necessary and started when necessary.

If a flow of liquid is actually realized between two part of the apparatus that are in liquid connection and thus liquid is flowing through the connecting line between the two parts, these two parts are in "fluid communication". Consequently, "fluid communication" according to the present invention describes the status in which a "fluid connection" is actually used by flowing liquid through the connecting line. If two parts of the system are partly in fluid communication it means that the fluid communication is not permanent and the liquid is not permanently flowing from one part to the other but only part of the time. Typically the flow of the liquid between two parts of the system is started and/or stopped with the aid of valves that direct the liquid flow.

A "fluid inlet" or "inlet" is any means that enables the introduction of liquid. A separation unit inlet is for example the end-fitting of a chromatography column to which a connecting line can be connected. An inlet can also be a valve that provides the introduction of liquid in a connecting line. A inlet can also be the end of a connecting line.

An "outlet" or "fluid outlet" is any means that enables the withdraw of a liquid. A separation unit outlet is for example the end-fitting of a chromatography column to which a connecting line can be connected. An outlet can also be a valve that provides the introduction of liquid in a connecting line. A outlet can also be the end of a connecting line.

A "fluid selection valve" is any means that enables a fluid communication selectively between any connected fluid and the system part. A fluid selection valve is for example the valve prior the separation unit inlet, to which the connecting lines can be connected and selectively chosen which can enable the fluid communication between the selected line and the separation unit inlet. A fluid selection valve is for example the valve after the separation unit outlet, to which the connecting lines can be connected and selectively chosen which can enable the fluid communication between the selected line and the separation unit outlet. A fluid selection valve can also be a valve that provides the introduction of liquid in a connecting line. A fluid selection valve can also be the end of a connecting line.

A "solvent selection valve" is a fluid selection valve that enables a fluid communication selectively between any connected solvent reservoir and the system part. A solvent selection valve is for example the valve prior the solvent pump, to which the connecting lines can be connected from the solvent reservoirs and selectively chosen which can enable the fluid communication between the selected solvent and the pump.

A "fluid selection valve" and "solvent selection valve" can be of identical type or of different type.

A solvent delivery system is a system that enable the delivery of liquid. Typically the solvent delivery system of an apparatus comprises at least one reservoir and at least one pump to transport the liquid from the reservoir to another part of the apparatus which is in liquid connection with the reservoir. It is known to a person skilled in the art that every time liquid is transferred from a reservoir to a separation unit this is done with the aid of a pump. The pumps can also be used to mix two or more liquid streams coming from two or more reservoirs.

The term "feed" refers to a liquid which contains two or more compounds to be separated. In this context, the term "compound" is used in a broad sense for any entity such as a molecule, chemical compound, cell etc. Typically, the feed is the sample containing the target molecule.

The term "break-through" means the point of time during feed addition to a chromatography matrix or separation unit such as a packed chromatography column when the compound that is adsorbed onto the matrix first appears in the outflow. In other words, the "break-through" is the point of time when loss of target compound begins.

The term "regeneration" means herein a process of treating a chromatography matrix to make it useful again in chromatography. Thus, "regeneration" will include release of bound compounds, also known as elution of compounds, as well as re-equilibration with the appropriate adsorption buffer. As will be discussed below, "regeneration" may also include cleaning in place (CIP).

The term "flow programming" means a deliberate change in feed flow rate during application of feed to a chromatography column.

The term "capture" means in the context of a chromatography method the first chromatography step, wherein a large amount of target compound is captured.

"Full binding" means the point in time when a chromatography matrix e.g. in a packed chromatography column has adsorbed so much of a target compound that it cannot adsorb more under the given conditions. Typically, full binding is reached when a matrix has adsorbed more than 60% of its original capacity estimated during corresponding static binding capacity measurements.

Loading time means the time required to saturate an adsorbent such as a packed chromatography column to its "full binding" state.

The term "average particle size diameter" or d50 means the average particle size distribution value at 50% of the cumulative particle size distribution.

The term "average pore size" means the average pore size distribution value at 50% of the cumulative pore size distribution.

The terms "clarify," "clarification," and "clarification step," as used herein, refers to a process step for removing suspended particles and or colloids, thereby to reduce turbidity, of a target molecule containing solution, as measured in NTU (nephelometric turbidity units). Clarification can be achieved by a variety of means, including centrifugation, settling or filtration. Centrifugation could be done in a batch or continuous mode, while filtration could be done in a normal flow (e.g. depth filtration) or tangential flow mode. In processes used in the industry today, centrifugation is typically followed by depth filters intended to remove insoluble impurities, which may not have been removed by centrifugation. Furthermore, methods for enhancing clarification efficiency can be used, e.g. precipitation. Precipitation of impurities can be performed by various means such as by flocculation, pH adjustment (acid precipitation), temperature shifts, phase change due to stimulus-responsive polymers or small molecules, or any combinations of these methods. In some embodiments described herein, clarification involves any combinations of two or more of centrifugation, filtration, depth filtration and precipitation. In some embodiments, the processes and systems described herein obviate the need for centrifugation.

The term "precipitate," precipitating" or "precipitation" as used herein, refers to process used in clarification, in which the properties of the undesirable impurities are modified such that they can be more easily separated from the soluble target molecule, e.g. by causing the precipitation of a compound from a soluble state to a non-soluble state or by agglutinating and/or aggregating fine particles from a solution so that their settling and/or filtration and/or centrifugation is improved and thus a reduction of the turbidity is reached. This is typically accomplished by forming large aggregate particles and/or insoluble complexes containing the undesirable impurities. These particles have properties (e.g. density or size) such that they can be more easily separated from the liquid phase that contains the soluble target molecule, such as by filtration or centrifugation. In some cases, a phase change is effected, such that the undesirable impurities can be more easily separated from the soluble target molecule. Precipitation by phase change can be effected by the addition of a precipitating agent, such as a polymer or a small molecule. In a particular embodiment, the precipitant is a stimulus responsive polymer, also referred to as a smart polymer. In some embodiments described herein, the precipitant or precipitating agent is a flocculant. Flocculation, as used herein, is one way of performing precipitation where the performance typically depends on the flocculant concentration used ("dose dependent"). Typical flocculating agents are polyelectrolytes, such as polycations, that complex with oppositely charged impurities.

In some embodiments described herein, clarification employs the addition of a precipitant to a sample containing a target molecule and one or more impurities. In some cases, a change in solution conditions (such as temperature, pH, salinity) may be used to initiate the precipitation, such as in the case of stimulus responsive polymers. The precipitated material which contains the one or more impurities as well as the precipitating agent is removed thereby recovering the target molecule in the liquid phase, where the liquid is then typically subjected to further process steps in order to further purify the target molecule.

Precipitation may be performed directly in a bioreactor containing a cell culture expressing a target molecule to be purified, where a precipitant is added directly to the bioreactor. Alternatively, the precipitant may be added to the cell culture, which typically contains the target molecule, in a separate vessel.

There are many ways known to those skilled in the art of removing the precipitated material, such as centrifugation, filtration or settling or any combinations thereof.

The term "settling," as used herein, refers to a sedimentation process in which the precipitated material migrates to the bottom of a vessel under the influence of gravitational forces. Settling can be followed by decanting and/or filtering of the liquid phase or supernatant.

The term "stimulus" or "stimuli," as used interchangeably herein, is meant to refer to a physical or chemical change in the environment which results in a response by a stimulus responsive polymer. Accordingly, such polymers are responsive to a stimulus and which stimulus results in a change in the solubility of the polymer. Examples of stimuli to which one or more polymers used herein are responsive, include, but are not limited to, e.g., changes in temperature, changes in conductivity and/or changes in pH. In some embodiments, a stimulus comprises addition of a complexing agent or a complex forming salt to a sample. In various embodiments, a stimulus is generally added after the addition of a polymer to a sample. Although, the stimulus may also be added during or before addition of a polymer to a sample.

The term "stimulus responsive polymer," as used herein, refers to a polymer or copolymer which exhibits a change in a physical and/or chemical property after the addition of a stimulus. A typical stimulus response is a change in the polymer's solubility. For example, the polymer poly(N-isopropylacrylamide) is water soluble at temperatures below about 35° C., but become insoluble in water at temperatures of about 35° C. In a particular embodiment, a stimulus responsive polymer is a polyallylamine or a polyvinylamine polymer which is responsive to a multivalent ion stimulus (e.g, phosphate stimulus).

In some embodiments, a cell culture is subjected to a depth filter to remove one or more impurities.

The terms "depth filter" or "depth filtration" as used herein refer to a filter that is capable of retaining particulate matter throughout the filter medium, rather than just on the filter surface. In some embodiments described herein, one or more depth filters are used in the clarification process step.

In some embodiments, clarification results in the removal of soluble and/or insoluble impurities in a sample which may later on result in the fouling of a filter or device used in a process step in a purification process, thereby making the overall purification process more economical.

The terms "flow-through process," "flow-through mode," and "flow-through operation," as used interchangeably herein, refer to a separation technique in which at least one target molecule (e.g., an Fc-region containing protein or an antibody) contained in a biopharmaceutical preparation along with one or more impurities is intended to flow through a material, which usually binds the one or more impurities, where the target molecule usually does not bind (i.e., flows through).

The terms "bind and elute mode" and "bind and elute process," as used herein, refer to a separation technique in which at least one target molecule contained in a sample (e.g., an Fc region containing protein) binds to a suitable resin or media (e.g., an affinity chromatography media or a cation exchange chromatography media) and is subsequently eluted.

DETAILED DESCRIPTION OF THE INVENTION

The present invention for the first time provides a method for a continuous chromatography process which allows to maintain high binding capacity at low residence time.

Therefore it is not only fast, but also an economical purification (capture) technology, usually increasing the productivity of the named step by a factor of >2. In our new, innovative methodology, the productivity (g (target molecule)/ml (packed bed)/h (production time) is usually in the range of 6-10 greater than the one of batch process.

Method

The method according to the present invention is based on the combination of a certain type of chromatography matrix with a certain type of continuous chromatography process.

The chromatography matrix to be used in the method according to the present invention is a particulate sorbent. The average sorbent particle size (d50) is between 30 and 200 µm. The pores have an average pore size between 40 nm and 300 nm.

In a preferred embodiment, the average size of the particles is between 40 and 120 µm, more preferably between 55 and 100 µm In another preferred embodiment, the particles have pores of average pore size in the range between 50 and 150 nm, most preferred between 60 and 100 nm.

Average pore size values and average particle size values are defined as the value where half of the population resides above this point, and half resides below this point. For particle size distributions the average pore size is called the d50.

The d50 is the size in microns that splits the distribution with half above and half below this diameter. D50 corresponds to 50% of the cumulative size distribution.

The standard methods for the particle size estimation can be imaging and image analysis, light scattering technologies, sieving technologies, sedimentation techniques, acoustic spectroscopy technologies and other. (K. K. Unger et al. "Particled packed columns and monolithic columns in high-performance liquid chromatography—comparison and critical appraisal" J. Chrom. A. 1184 (2008) 393-415). The used characterization method given for the average particle diameter value estimation was light scattering. According to the present invention, laser diffraction is used for particles with diameters up to 30 nm and single-particle optical sensing (SPOS) is used for particles with diameters between 0.5 nm-400 nm.

The pore size can be measured by the inversive size exclusion chromatography, mercury intrusion, gas adsorption technologies, etc. (M. Thommes et al., "Textural characterization of native and n-alky-bonded silica monoliths by mercury intrusion/extrusion, inverse size exclusion chromatography and nitrogen sorption", J. Chrom. A, 2008).

The pore volume can be estimated by the same methods, used for the pore size estimation. According to the present invention, for the average pore size estimation and the average pore volume estimation inverse size exclusion chromatography is used for matrices which cannot be measured in the dry state as their physical properties change when the matrices are dried. For matrices which can be measured in the dry state the nitrogen adsorption methods are used.

The particles can be regularly or irregularly formed. They can be made of any material suitable as chromatographic sorbent, like polysaccharides (such as agarose and cellulose); and other mechanically stable matrices such as silica (e.g. controlled pore glass), poly(styrenedivinyl)benzene, polyacrylamide, polymethacrylates, ceramic particles or copolymers of hydrophilically substituted alkyl vinyl ethers like 1,2-ethanediol monovinyl ether, 1,3-propanediol monovinyl ether, 1,4-butanediol monovinyl ether, 1,5-pentanediol monovinyl ether, 1,6-hexanediol monovinyl ether, diethylene glycol monovinyl ether or cyclohexanedimethanol monovinyl ether and crosslinking agents like divinylethyleneurea (1,3-divinylimidazolin-2-one) or divinylpropyleneurea (1,3-divinyltetrahydropyrimidin-2-one) and derivatives of any of the above. Examples of copolymers of hydrophilically substituted alkyl vinyl ethers are disclosed in EP 1910433. Preferred are materials which show a high rigidity so that velocities above 1000 cm/h can be applied.

As the method according to the present invention is preferably based on affinity or ion exchange chromatography, the particles to be used as chromatography matrix typically carry affinity ligands like Protein A or a functional variant thereof or ion exchange ligands.

The method according to the present invention is based on the use of at least three separation units having the same chromatography matrix which are connected so that liquid can at least flow from one separation unit to the subsequent one and from the last to the first separation unit. That means, all separation units of the system are connected in a circle (FIG. 1).

Figure 3A:
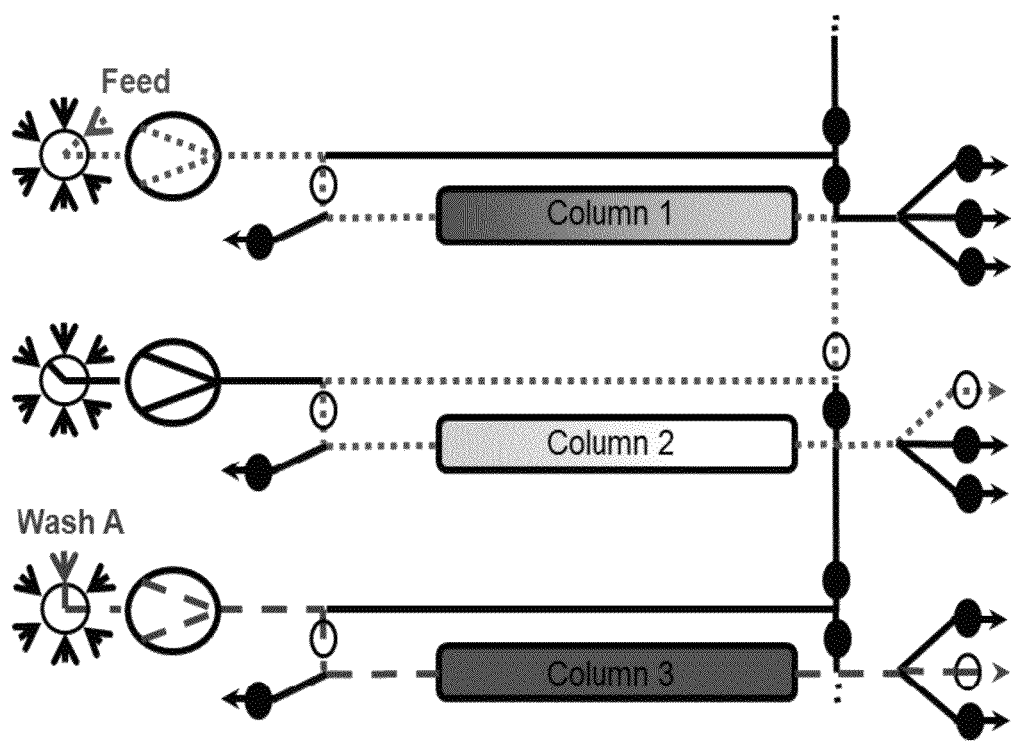
FIGS. 3a-c schematically shows a selected part of the three column continuous process for the highlighted fluid communication during the loading phase, where in a) separation unit 1 is in fluid communication with separation unit 2 during the loading and separation unit 3 is in washing phase, b) separation unit 2 is in fluid communication with separation unit 3 and separation unit 1 is in washing phase, c) separation unit 3 is in the fluid communication with separation unit 1 and separation unit 2 is in washing phase.
Figure 3B:
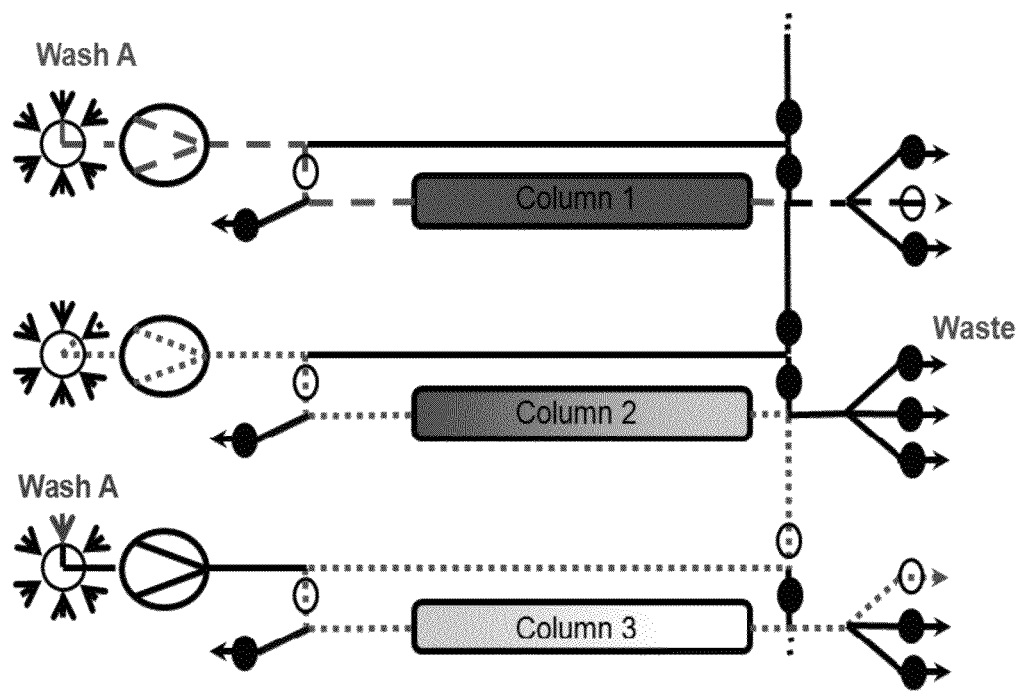

The method comprises the steps of:
a) providing at least three separation units having the same matrix, preferably an affinity or ion exchange chromatography matrix, which are connected so that liquid can flow from one separation unit to the subsequent one and from the last to the first separation unit;
b) feeding the sample on a first separation unit so that while the sample is loaded on this separation unit wherein the sample is at a pH and conductivity enabling the target molecules to be bound to this separation unit, said separation unit is at least part of the loading time in fluid communication with the next separation unit so that target molecules not bound to said first separation unit can bind to the next separation unit (FIG. 2a), at the same time at least eluting (FIG. 2c), and reequilibrating (FIG. 2e) one separation unit different from the separation unit that is loaded and from the one that is in fluid communication with the separation unit that is loaded. That means that the other process steps like washing, eluting and reequilibrating that are needed in a chromatographic separation process are performed on one or more of those separation units that are not in fluid communication with the separation unit or units that are being loaded.

c) switching the feed to the next separation unit. That means when the separation unit that has just been loaded is fully loaded, the sample feed to this separation unit is stopped and by simultaneous handling of the valves of the system without interruption directed to the separation unit that is next in the circle (FIG. 3b). The separation unit that is next in the circle is the one which was before at least part of the loading time connected to the outlet of the separation unit that has been loaded. Consequently, this separation unit is already partly loaded with those target molecules that have not been bound to the first separation unit.

d) feeding the sample on the next separation unit so that while the sample is loaded on said next separation unit wherein the sample is at a pH and conductivity enabling the target molecules to be bound to said next separation unit, said next separation unit is at least part of the loading time in fluid communication with the separation unit after the next so that target molecules not bound to said next separation unit can bind to the separation unit after the next, at the same time at least eluting and reequilibrating one separation unit different from the separation unit that is loaded and from the one that is in fluid communication with the separation unit that is loaded e) repeating steps c) and d) one or more times, During the time in which the continuous method according to the present invention is performed, the feed never stops and has a velocity above 800 cm/h. Preferably it has a velocity above 1000 cm/h.

And the chromatography matrix of the separation units comprises particles with an average particle diameter between 30 and 200 μm with average pore diameters in the range between 40 nm and 300 nm.

In a preferred embodiment additional washing step can be done (FIG. 2b) to wash the contaminants from the separation unit.

In a preferred embodiment the washing is done in two or more steps with two or more different washing buffers. For example, a first washing step with a first washing buffer can be used to wash unbound or weakly bound target molecule from the separation unit (FIG. 2a) and a second washing step using a second washing buffer can be used to wash contaminants from the separation unit (FIG. 2b).

In a preferred embodiment the solution containing unbound or weakly bound target molecule, usually during the washing phase can be redirected to the feedstock solution or to a dedicated outlet.

In a preferred embodiment the solution containing unbound or weakly bound target molecule, usually during the washing phase can be redirected to another separation unit.

In another preferred embodiment the cleaning in place is performed (FIG. 2d) after elution of the bound target molecule and before the reequilibration steps.

Figure 4:
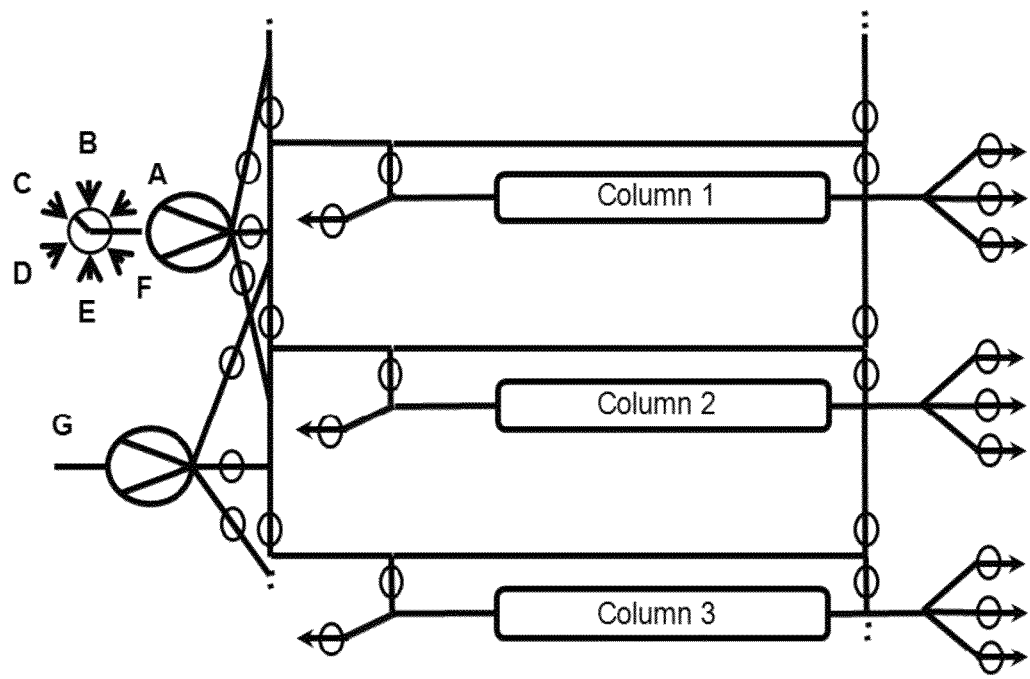
FIG. 4 shows a setup that is mainly restricted to the essential features of three separation units and two solvent delivery systems.

In another preferred embodiment a single solvent delivery system can be dedicated for feed delivery (FIG. 4).

In a preferred embodiment, the separation unit that is loaded with the target molecule is loaded to the maximum at the given conditions, that means it is loaded to full binding.

In one embodiment of the present invention, the separation unit that is loaded with the target molecule is over the whole loading time in fluid communication with another separation unit.

In another embodiment, the separation unit that is loaded is only part of the loading time in fluid communication with another separation unit. In a preferred embodiment, the said two separation units are only in fluid communication during the whole or parts of the second half of the loading time. This is due to the fact, that when loading starts, typically all target molecules are bound to the separation unit that is loaded. Only when this separation unit is already partly loaded, it might happen that target molecules are not bound and pass through the separation unit. In batch chromatography, typically, loading is stopped when too many target molecules start to pass through the separation unit. In the method according to the present invention, at least during this last phase of loading when the target molecules start to pass through the separation unit without being bound, the outlet of said separation unit is connected with the inlet of another separation unit so that the target molecule that has not bound to the first separation unit is bound to the second. A person skilled in the art can easily determine when during loading the amount of target molecule that is not bound to the separation unit that is loaded is that high that the outlet of said separation unit needs to be connected to the inlet of another separation unit.

In one embodiment, the outlet of the separation unit or the separation units that are washed is in liquid communication with the inlet of another separation unit so that target molecules removed by said washing are not lost but loaded onto the other separation unit. This approach is especially suitable when the system comprises 4 or more separation units.

In one embodiment, the outlet of the separation unit or the separation units that are washed is in a liquid communication with the previous separation unit so that target molecules removed by said washing are not lost but loaded onto the previous separation unit.

Figure 5A:
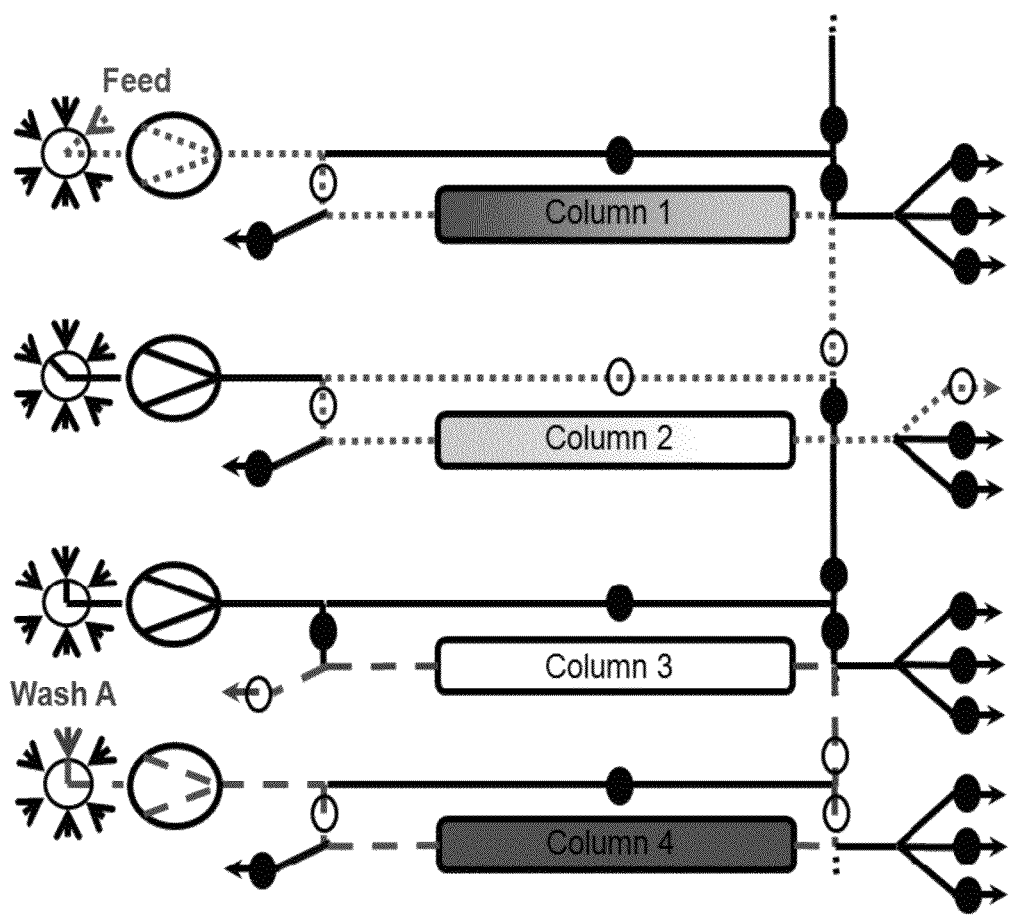
FIGS. 5a-d schematically shows a selected part of the four column continuous process for the highlighted fluid communication during the loading phase, where in a) separation unit 1 is in fluid communication with separation unit 2 during the loading and separation unit 4 is in fluid communication with separation unit 3 for the washing phase, b) separation unit 2 is in fluid communication with separation unit 3 and separation unit 1 is in fluid communication with separation unit 4 for the washing phase, c) separation unit 3 is in the fluid communication with separation unit 4 and separation unit 2 is in fluid communication with separation unit 1 for the washing phase, d) separation unit 4 is in the fluid communication with separation unit 1 and separation unit 3 is in fluid communication with separation unit 2 for the washing phase.
Figure 6A:
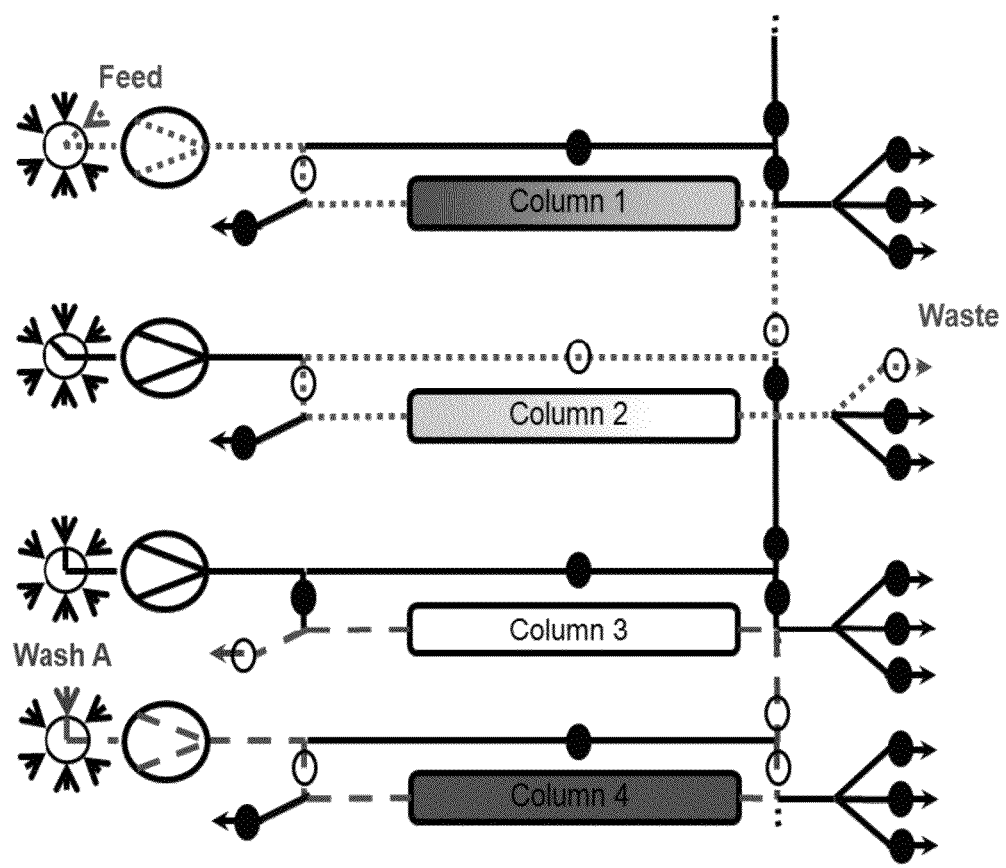
FIGS. 6a-e schematically shows a part of the four column continuous process, where first and second separation units are in fluid communication during the loading phase (feed) and the forth separation unit, different from the separation unit that is loaded and from the one that is in fluid communication with the separation unit that is loaded, is undergoing various process sub-steps: a) washing with solution A and transferring the so said wash solution from this separation unit to the previous that is in the fluid communication with a separation unit that is being washed, b) washing with solution B, c) eluting the bound target molecule, d) cleaning in place and e) regenerating the separation unit.

In one embodiment, such method comprises a) providing at least four separation units having the same affinity or ion exchange chromatography matrix which are connected so that liquid can flow from one separation unit to the subsequent one and from the last to the first separation unit;

b) feeding the sample on a first separation unit so that while the sample is loaded on this separation unit wherein the sample is at a pH and conductivity enabling the target molecules to be bound to this separation unit, said separation unit is at least part of the loading time in fluid communication with the next separation unit so that target molecules not bound to said first separation unit can bind to the next separation unit (FIG. 5a), at the same time at least washing one separation unit that is in a liquid communication with the previous separation unit so that target molecules removed by said washing are not lost but loaded onto the previous separation unit (FIG. 6a). Then sequentially eluting (FIG. 6c), and reequilibrating (FIG. 6e) one separation unit different from the separation unit that is loaded and from the one that is in fluid communication with the separation unit that is loaded. That means that the other process steps like washing, eluting and reequilibrating that are needed in a chromatographic separation process are performed on one or more of those separation units that are not in fluid communication with the separation unit or units that are being loaded.

c) switching the feed to the next separation unit. That means when the separation unit that has just been loaded is fully loaded, the sample feed to this separation unit is stopped and by simultaneous handling of the valves of the system without interruption directed to the separation unit that is next in the circle (FIG. 5b). The separation unit that is next in the circle is the one which was before at least part of the loading time connected to the outlet of the separation unit that has been loaded. Consequently, this separation unit is already partly loaded with those target molecules that have not been bound to the first separation unit.

d) feeding the sample on the next separation unit so that while the sample is loaded on said next separation unit wherein the sample is at a pH and conductivity enabling the target molecules to be bound to said next separation unit, said the next separation unit is at least part of the loading time in fluid communication with after the next separation unit so that target molecules not bound to said first separation unit can bind to the after the next separation unit (FIG. 6b), at the same time at least washing one separation unit that is in a liquid communication with the previous separation unit so that target molecules removed by said washing are not lost but loaded onto the previous separation unit. Then sequentially eluting, and reequilibrating one separation unit different from the separation unit that is loaded and from the one that is in fluid communication with the separation unit that is loaded. That means that the other process steps like washing, eluting and reequilibrating that are needed in a chromatographic separation process are performed on one or more of those separation units that are not in fluid communication with the separation unit or units that are being loaded.

e) repeating steps c) and d) one or more times,

The process described above in steps b) to e) and illustrated in FIG. 6 can also be performed by connecting three separation units for loading. That means that if e.g. separation unit 1 is loaded, it is in fluid communication with separation unit 2 and separation unit 3 is in fluid communication with separation unit 2 but separation unit 1, 2 and 3 are during this time not in fluid communication with separation unit 4. When separation units 1, 2 and 3 are in fluid communication and are loaded, separation unit 4 is typically in a stand by mode. A person skilled in the art can decide based on the specific process parameters like type of matrix, type of sample, flow rate etc. whether it is favourable to connect three separation units for loading or only two. FIG. 1 schematically shows the three separation unit system, suitable for the continuous chromatography method described below. The system has solvent delivery systems (at least two as indicated in FIG. 4), three separation units, fluid communication channels between the solvent delivery systems and separation units, separation unit inlets and outlets, switching valves to redirect the solvent flow to the separation unit and from the separation unit. Optionally the FIG. 1 shows solvent selection valves prior solvent delivery systems to select the necessary solvent for the required process step or sub-step. A person skilled in the art can decide based on the specific process parameters like type of the solvent delivery systems, separation units and means to control solvent flow etc. based on selected application and requirements thereof.

Figure 2A:
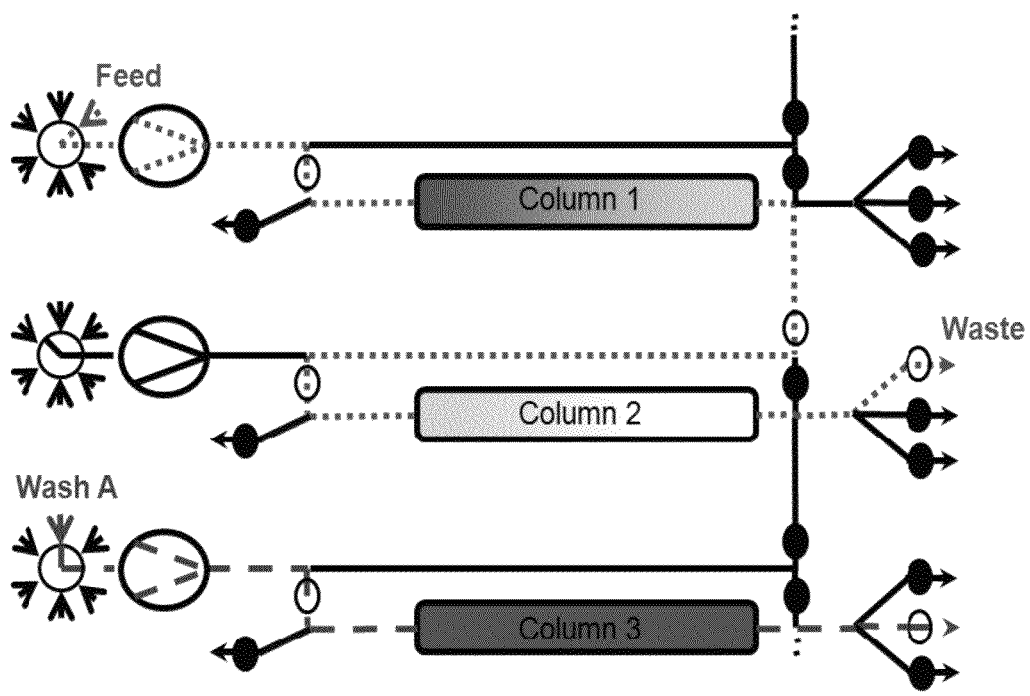
FIGS. 2a-e schematically shows a part of the three column continuous process, where first and second separation units are in fluid communication during the loading phase (feed) and the third separation unit, different from the separation unit that is loaded and from the one that is in fluid communication with the separation unit that is loaded, is undergoing various process sub-steps: a) washing with solution A, b) washing with solution B, c) eluting the bound target molecule, d) cleaning in place and e) regenerating the separation unit.
Figure 2B:
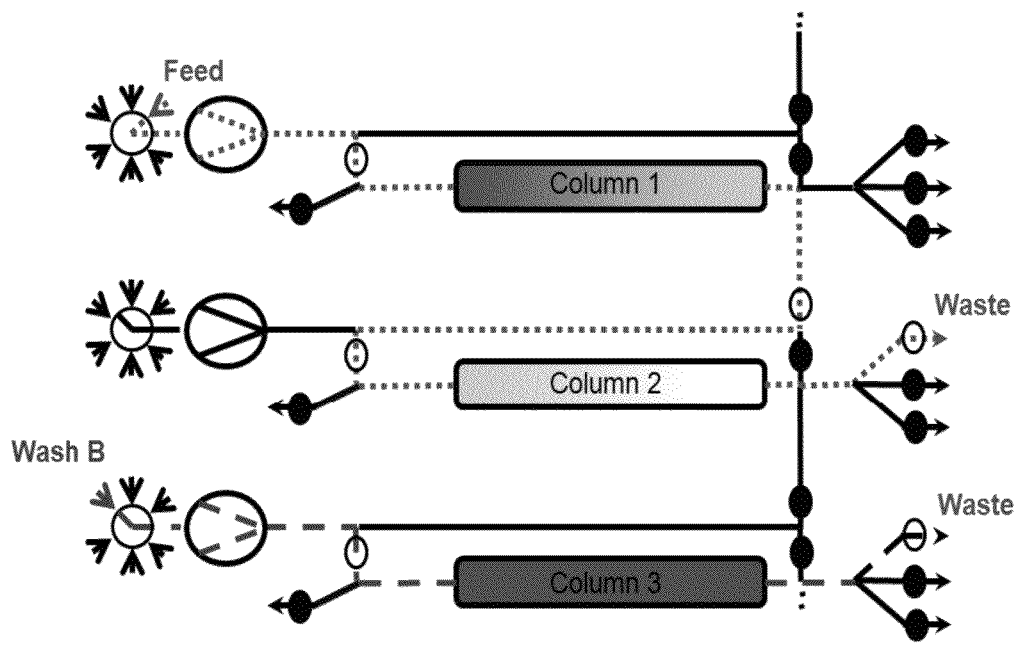
Figure 2C:
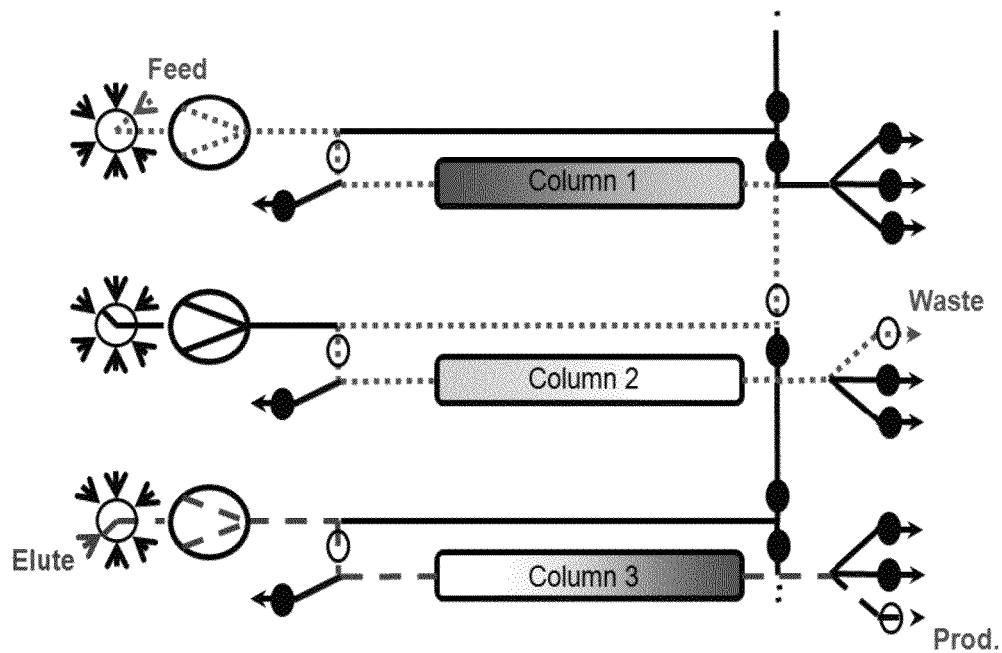
Figure 2D:
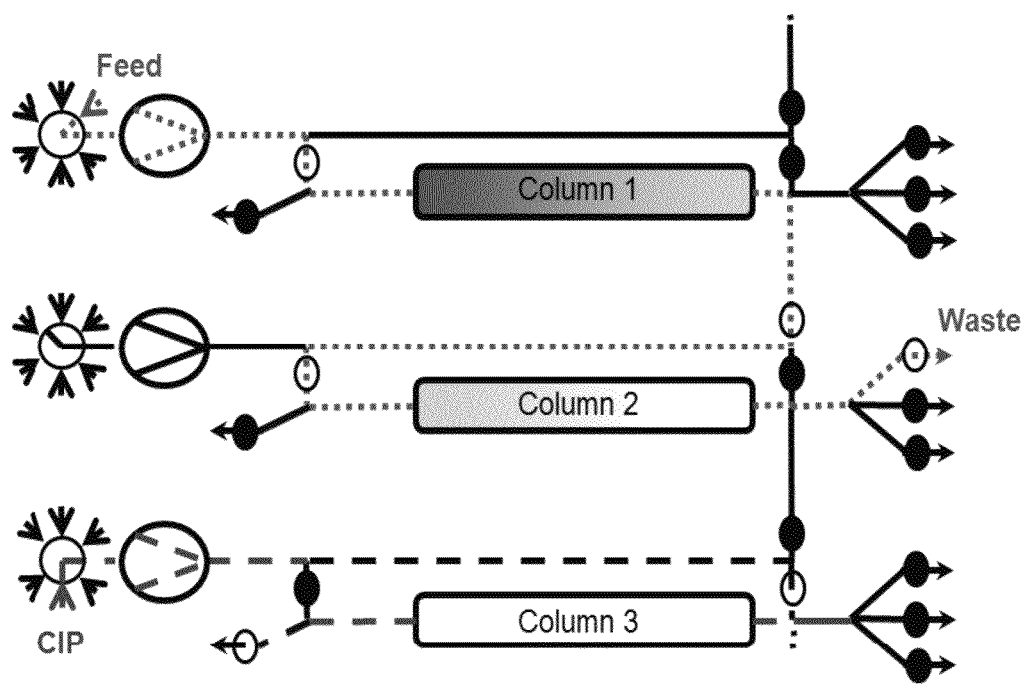
Figure 2E:
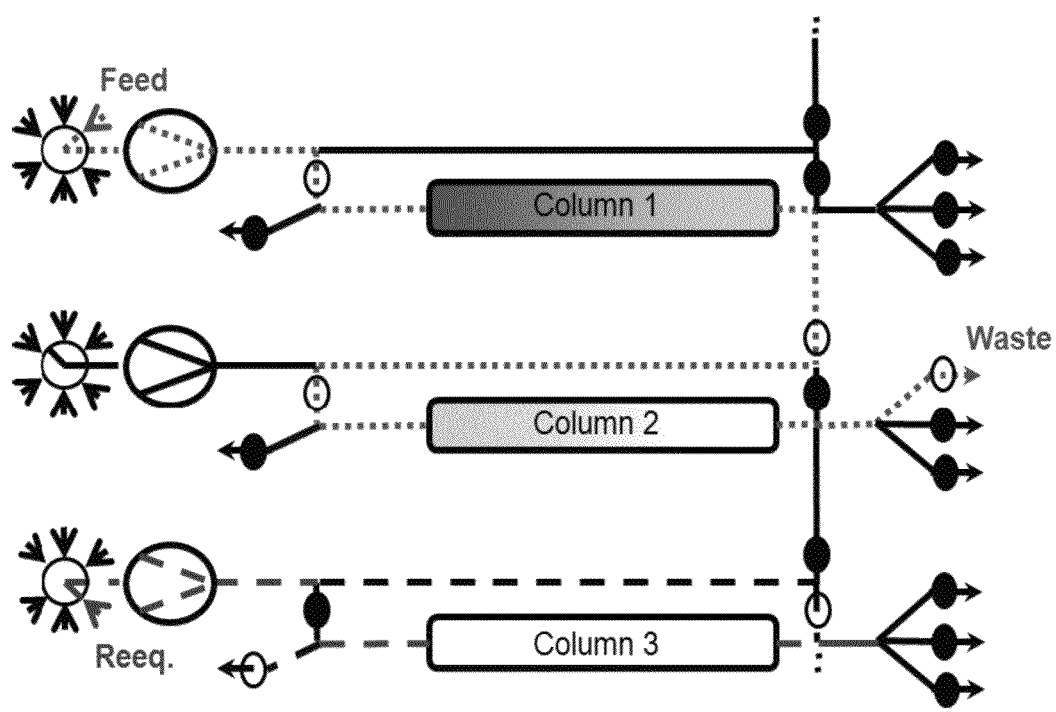

FIG. 2a-e schematically shows the steps of the method according to the present invention with a three column system. In FIG. 2a the feed has been switched to the inlet of separation unit 1, flows through separation unit 1, whereby at least part of the target molecules are bound to separation unit 1. The outlet of separation unit 1 is in liquid communication with the inlet of separation unit 2 so that all parts of the feed that have not bound to separation unit 1 are additionally passed through separation unit 2. This enables target molecules that have not bound to separation unit 1 to bind to separation unit 2. The outlet of separation unit 2 is connected to the waste. While loading separation unit 1 and 2, separation unit 3 which has been loaded before is e.g. washed (FIG. 2a and FIG. 2b), eluted (FIG. 2c), undergoes cleaning in place (FIG. 2d) and reequlibration (FIG. 2e) and all other process steps that might be necessary and are different from loading. The outlet of the separation unit 3 can be connected to a collecting tank or to another unit where the weakly bound or unbound target molecule removed by said wash is further processed (FIG. 2a). As long as the target molecule is eluted from separation unit 3 the outlet of separation unit 3 is connected to a target molecule collecting tank (indicated with "product" in FIG. 2c) or to another unit where the target molecule is further processed (not shown in FIG. 2c). For other process steps, the outlet of separation unit 3 is connected to one of the outlets as shown in FIG. 2b, FIG. 2d and FIG. 2e. Optionally, clean in place and reequilibrate steps on separation unit 3 can be performed a reversed flow mode as shown in FIG. 2d and FIG. 2e. In a next step that is shown in FIG. 3b, the feed is switched to the inlet of separation unit 2 and flows through separation unit 2, whereby at least part of the target molecules are bound to separation unit 2. The outlet of separation unit 2 is in liquid communication with the inlet of separation unit 3 so that all parts of the feed that have not bound to separation unit 2 are additionally passed through separation unit 3. This enables target molecules that have not bound to separation unit 2 to bind to separation unit 3. The outlet of separation unit 3 is connected to the waste. While loading separation unit 2 and 3, separation unit 1 which has been loaded before is e.g. washed, eluted, undergoes cleaning in place and reequilibration and all other process steps that might be necessary and are different from loading. The outlet of the separation unit 1 can be connected to a collecting tank or to another unit where the weakly bound or unbound target molecule removed by said wash is further processed. As long as the target molecule is eluted from separation unit 1 the outlet of separation unit 1 is connected to a target molecule collecting tank or to another unit where the target molecule is further processed. For other process steps, the outlet of separation unit 1 is connected to one of the outlets. Optionally, clean in place and reequilibrate steps on separation unit 1 can be performed a reversed flow mode.

Figure 3C:
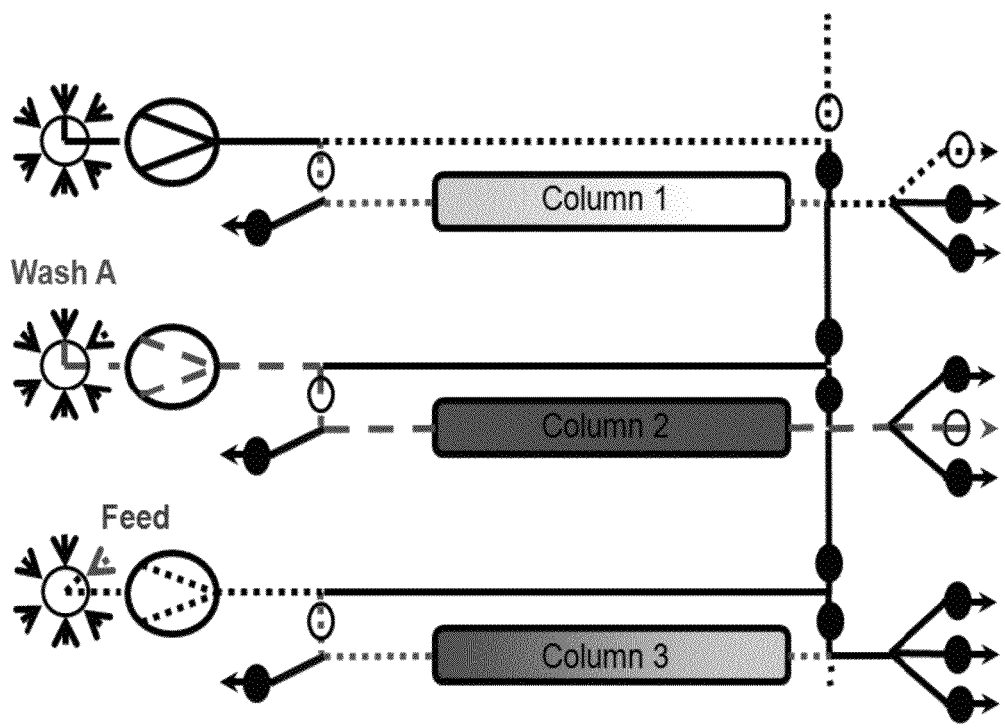

In a next step that is shown in FIG. 3c, the feed is switched to the inlet of separation unit 3 and flows through separation unit 3, whereby at least part of the target molecules are bound to separation unit 3. The outlet of separation unit 3 is in liquid communication with the inlet of separation unit 1 so that all parts of the feed that have not bound to separation unit 3 are additionally passed through separation unit 1. This enables target molecules that have not bound to separation unit 3 to bind to separation unit 1. The outlet of separation unit 1 is connected to the waste. While loading separation unit 3 and 1, separation unit 2 which has been loaded before is e.g. washed, eluted, undergoes cleaning in place and reequlibration and all other process steps that might be necessary and are different from loading. The outlet of the separation unit 2 can be connected to a collecting tank or to another unit where the weakly bound or unbound target molecule removed by said wash is further processed. As long as the target molecule is eluted from separation unit 2 the outlet of separation unit 2 is connected to a target molecule collecting tank or to another unit where the target molecule is further processed. For other process steps, the outlet of separation unit 2 is connected to one of the outlets. Optionally, clean in place and reequilibrate steps on separation unit 2 can be performed a reversed flow mode.

In the next step, the feed is again switched to separation unit 1 (FIG. 3a) and the process step as described in FIG. 2a-e is performed again. Typically, the process steps are performed more than two times. As can be seen from the description of the process shown in FIGS. 2a-e and FIG. 3 a-c, the feed never stops and in each process step (one process step is shown in FIG. 2a-e), target molecule is eluted from at least one separation unit.

In another embodiment of the present invention the wash liquid that is used for washing the loaded separation unit to remove unbound or weakly bound target molecules, when being eluted form the loaded separation unit, is not directed to selected system outlet but to the inlet of another separation unit. This ensures that target molecules that might be eluted from the loaded separation unit during washing does not go to outlet but is bound onto another separation unit.

Figure 6B:
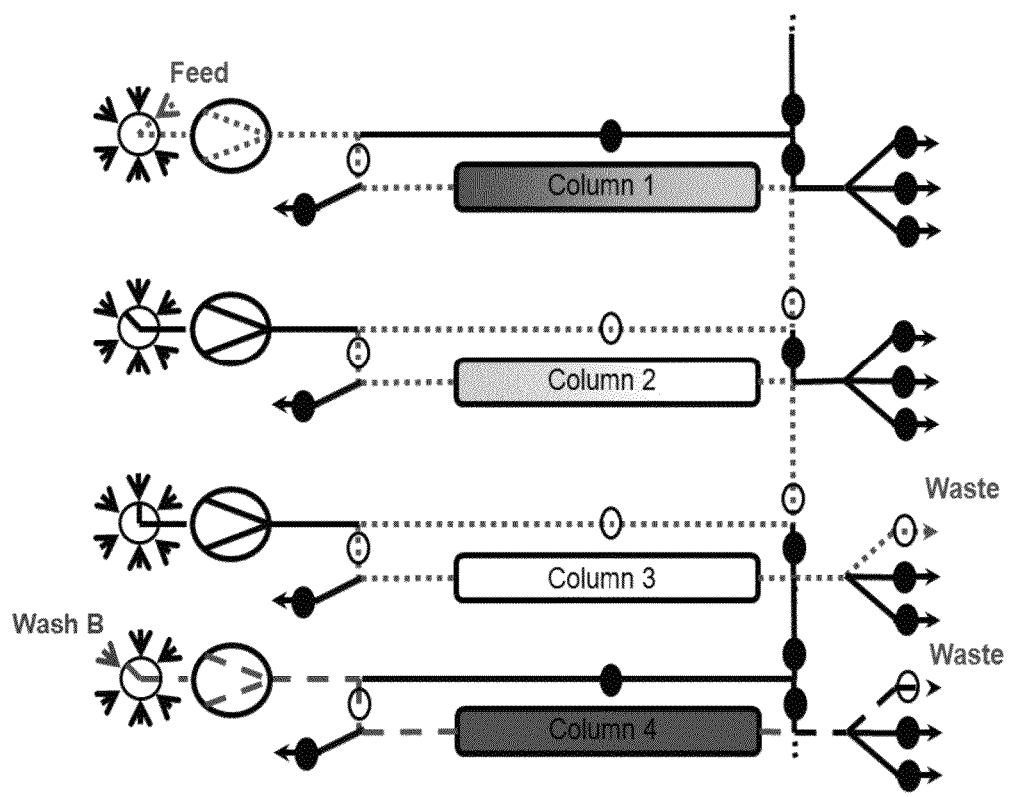
Figure 6C:
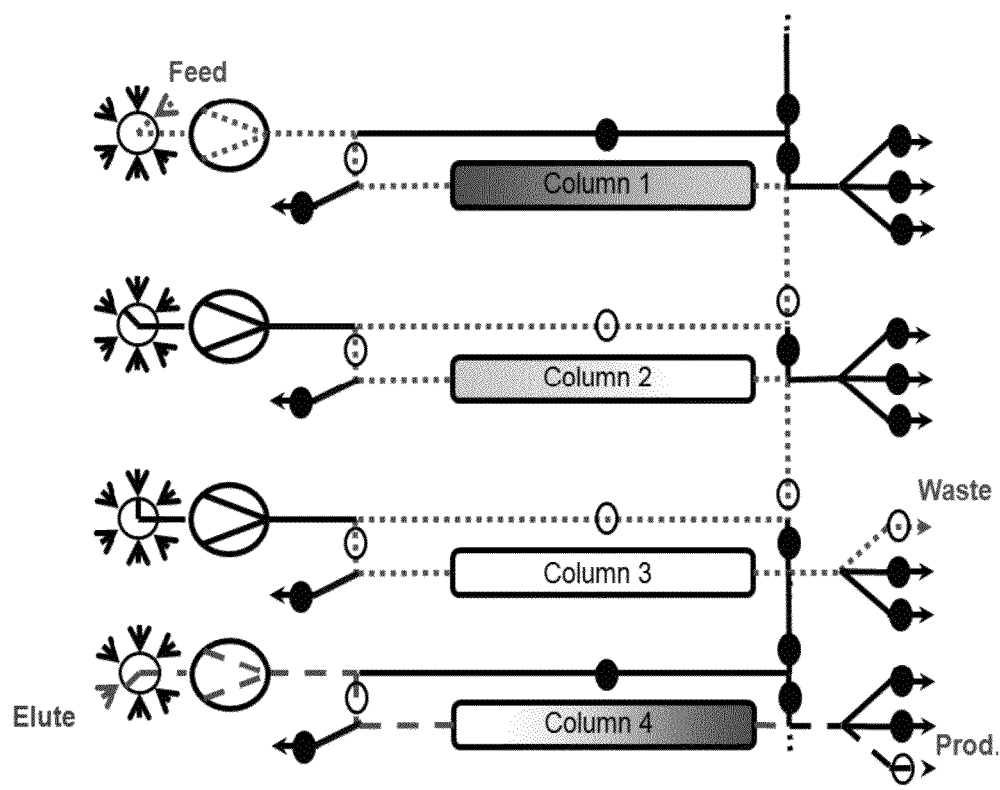
Figure 6D:
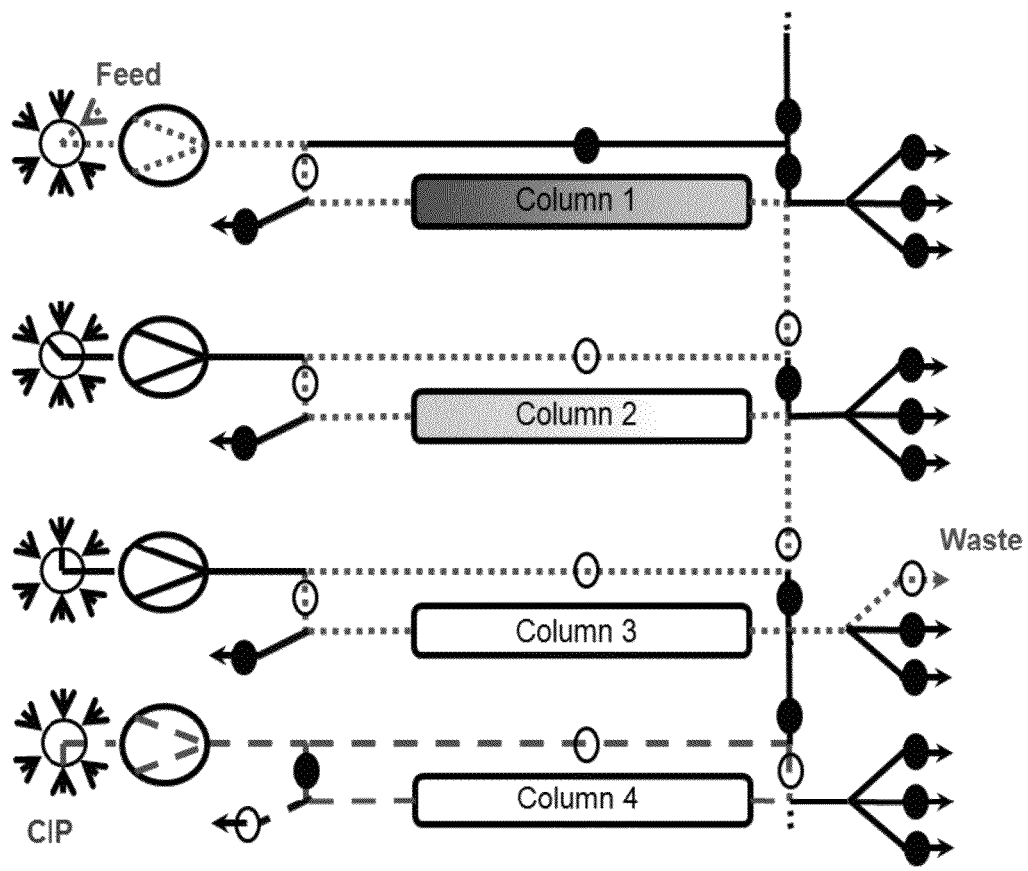
Figure 6E:
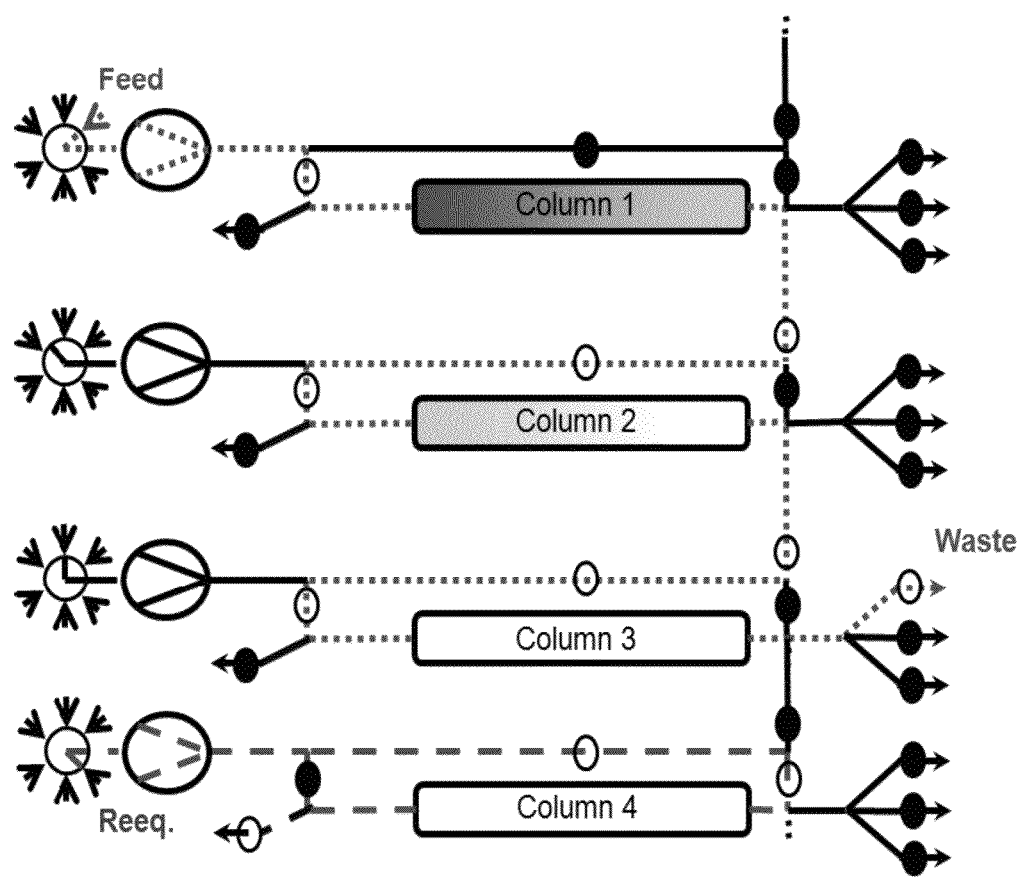

FIG. 6a-e schematically shows the steps of the method according to the present invention with a four column system. In FIG. 6a the feed has been switched to the inlet of separation unit 1, flows through separation unit 1, whereby at least part of the target molecules are bound to separation unit 1. The outlet of separation unit 1 is in liquid communication with the inlet of separation unit 2 so that all parts of the feed that have not bound to separation unit 1 are additionally passed through separation unit 2. This enables target molecules that have not bound to separation unit 1 to bind to separation unit 2. The outlet of separation unit 2 is connected to the waste. While loading separation unit 1 and 2, separation unit 4 which has been loaded before is e.g. washed (FIG. 6a and FIG. 6b), eluted (FIG. 6c), undergoes cleaning in place (FIG. 6d) and reequlibration (FIG. 6e) and all other process steps that might be necessary and are different from loading. During the washing phase or a part of the washing phase of separation unit 4, the outlet of the separation unit 4 is in fluid communication with the separation unit 3 where the weakly bound or unbound target molecule removed by said wash, and not bound to the separation unit 4 are additionally passed through the separation unit 3. This enables target molecules that have not bound to separation unit 4 to bind to separation unit 3 (FIG. 6a). Additionally the outlet of the separation unit 4 can be in fluid communication with the inlet of the separation unit 3 (not shown in FIG. 6a) or with outlet of the separation unit 3 (FIG. 6a). Furthermore, the separation unit 3 can be in fluid communication with separation unit 2 (FIG. 6b-e). As long as the target molecule is eluted from separation unit 4 the outlet of separation unit 4 is connected to a target molecule collecting tank (indicated with "product" in FIG. 6c) or to another unit where the target molecule is further processed (not shown in FIG. 6c). For other process steps, the outlet of separation unit 4 is connected to one of the outlets as shown in FIG. 6b, FIG. 6d and FIG. 6e. Optionally, clean in place and reequilibrate steps on separation unit 4 can be performed a reversed flow mode as shown in FIG. 4d and FIG. 4e.

In a next step that is shown in FIG. 5b, the feed has been switched to the inlet of separation unit 2, flows through separation unit 2, whereby at least part of the target molecules are bound to separation unit 2. The outlet of separation unit 2 is in liquid communication with the inlet of separation unit 3 so that all parts of the feed that have not bound to separation unit 2 are additionally passed through separation unit 3. This enables target molecules that have not bound to separation unit 2 to bind to separation unit 3. The outlet of separation unit 3 is connected to the waste. While loading separation unit 2 and 3, separation unit 1 which has been loaded before is e.g. washed, eluted, undergoes cleaning in place and reequlibration and all other process steps that might be necessary and are different from loading. During the washing phase or a part of the washing phase of separation unit 1, the outlet of the separation unit 1 is in fluid communication with the separation unit 4 where the weakly bound or unbound target molecule removed by said wash, and not bound to the separation unit 1 are additionally passed through the separation unit 4. This enables target molecules that have not bound to separation unit 1 to bind to separation unit 4. Additionally the outlet of the separation unit 1 can be in fluid communication with the inlet of the separation unit 4 or with outlet of the separation unit 4. Furthermore, the separation unit 4 can be in fluid communication with separation unit 3. As long as the target molecule is eluted from separation unit 1 the outlet of separation unit 1 is connected to a target molecule collecting tank or to another unit where the target molecule is further processed. For other process steps, the outlet of separation unit 1 is connected to one of the outlets. Optionally, clean in place and reequilibrate steps on separation unit 1 can be performed as reversed flow mode.

Figure 5B:
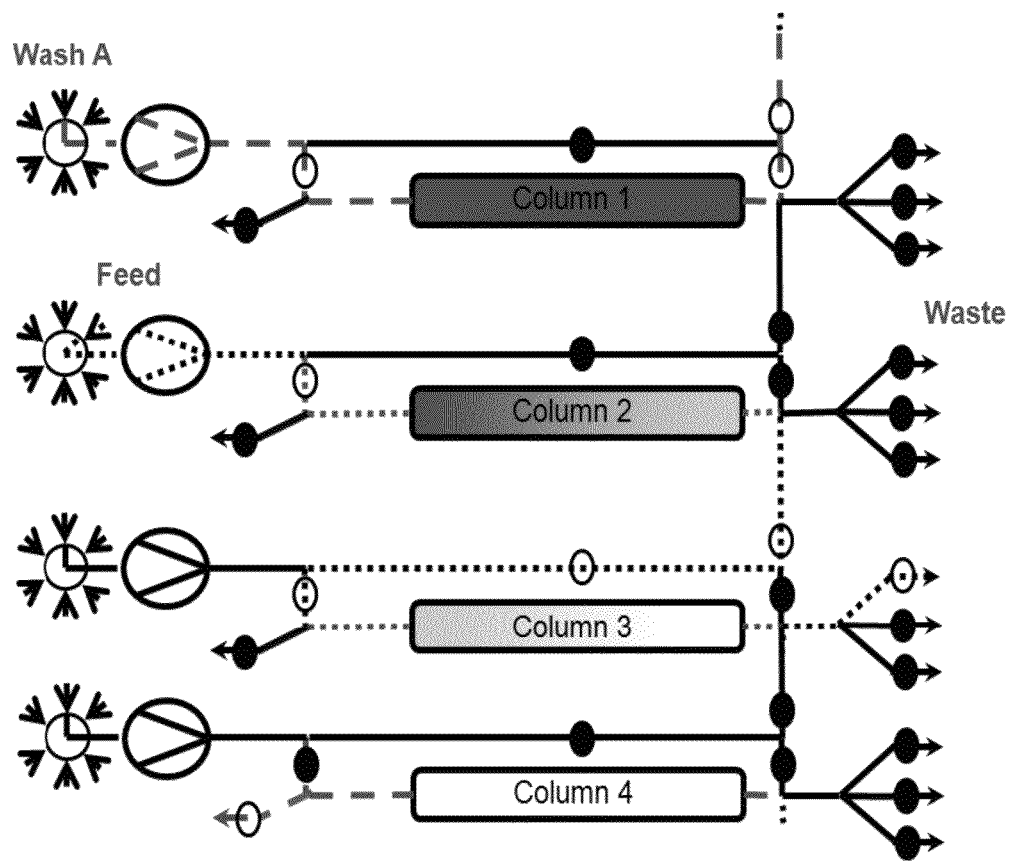
Figure 5C:
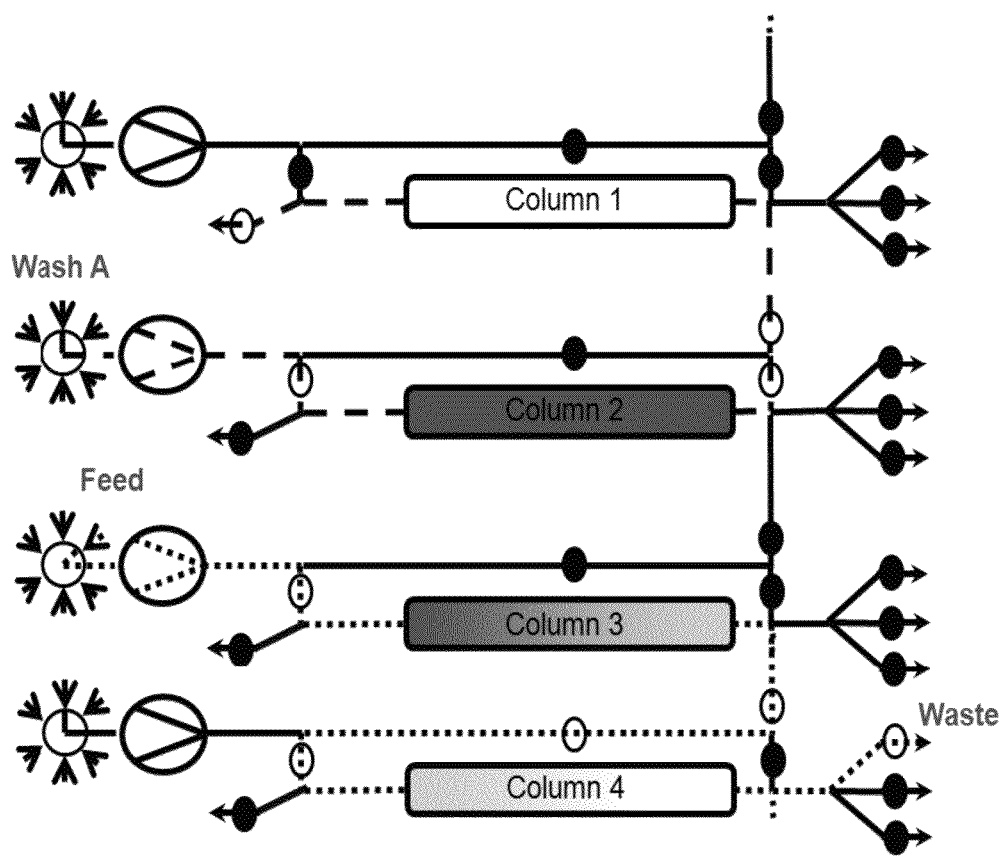

In a next step that is shown in FIG. 5c, the feed has been switched to the inlet of separation unit 3, flows through separation unit 3, whereby at least part of the target molecules are bound to separation unit 3. The outlet of separation unit 3 is in liquid communication with the inlet of separation unit 4 so that all parts of the feed that have not bound to separation unit 3 are additionally passed through separation unit 4. This enables target molecules that have not bound to separation unit 3 to bind to separation unit 4. The outlet of separation unit 4 is connected to the waste. While loading separation unit 3 and 4, separation unit 2 which has been loaded before is e.g. washed, eluted, undergoes cleaning in place and reequlibration and all other process steps that might be necessary and are different from loading. During the washing phase or a part of the washing phase of separation unit 2, the outlet of the separation unit 2 is in fluid communication with the separation unit 1 where the weakly bound or unbound target molecule removed by said wash, and not bound to the separation unit 2 are additionally passed through the separation unit 1. This enables target molecules that have not bound to separation unit 2 to bind to separation unit 1. Additionally the outlet of the separation unit 2 can be in fluid communication with the inlet of the separation unit 1 or with outlet of the separation unit 1. Furthermore, the separation unit 1 can be in fluid communication with separation unit 4. As long as the target molecule is eluted from separation unit 2 the outlet of separation unit 2 is connected to a target molecule collecting tank or to another unit where the target molecule is further processed. For other process steps, the outlet of separation unit 2 is connected to one of the outlets. Optionally, clean in place and reequilibrate steps on separation unit 2 can be performed in a reversed flow mode.

Figure 5D:
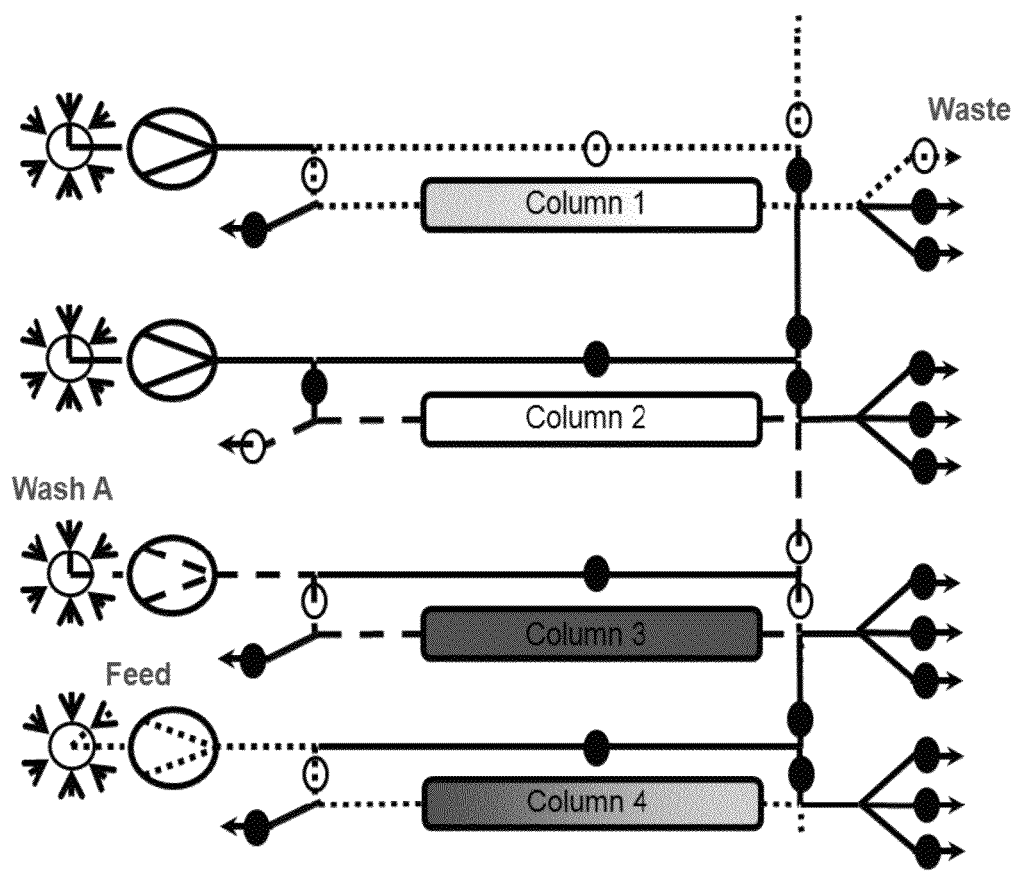

In a next step that is shown in FIG. 5d, the feed has been switched to the inlet of separation unit 4, flows through separation unit 4, whereby at least part of the target molecules are bound to separation unit 4. The outlet of separation unit 4 is in liquid communication with the inlet of separation unit 1 so that all parts of the feed that have not bound to separation unit 4 are additionally passed through separation unit 1. This enables target molecules that have not bound to separation unit 4 to bind to separation unit 1. The outlet of separation unit 1 is connected to the waste. While loading separation unit 4 and 1, separation unit 3 which has been loaded before is e.g. washed, eluted, undergoes cleaning in place and reequlibration and all other process steps that might be necessary and are different from loading. During the washing phase or a part of the washing phase of separation unit 3, the outlet of the separation unit 3 is in fluid communication with the separation unit 2 where the weakly bound or unbound target molecule removed by said wash, and not bound to the separation unit 3 are additionally passed through the separation unit 2. This enables target molecules that have not bound to separation unit 3 to bind to separation unit 2. Additionally the outlet of the separation unit 3 can be in fluid communication with the inlet of the separation unit 2 or with outlet of the separation unit 2. Furthermore, the separation unit 2 can be in fluid communication with separation unit 1. As long as the target molecule is eluted from separation unit 3 the outlet of separation unit 3 is connected to a target molecule collecting tank or to another unit where the target molecule is further processed. For other process steps, the outlet of separation unit 3 is connected to one of the outlets. Optionally, clean in place and reequilibrate steps on separation unit 3 can be performed in a reversed flow mode.

In the next step, the feed is again switched to separation unit 1 (FIG. 5a) and the process step as described in FIG. 6a-e is performed again. Typically, the process steps are performed more than two times.

Figure 7A:
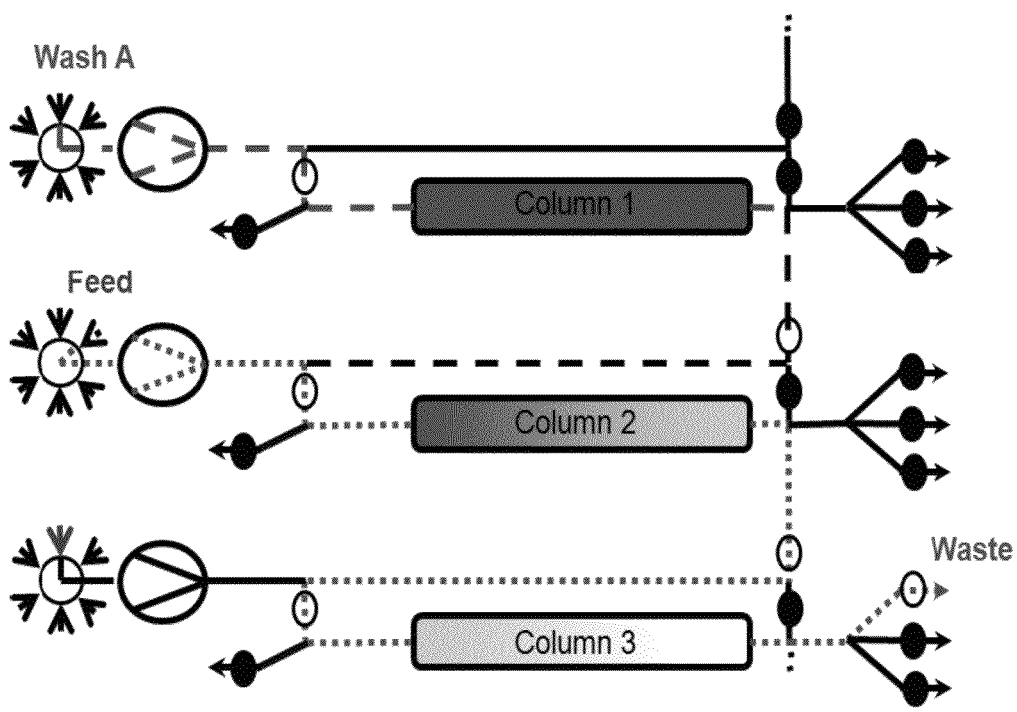
Figure 7B:
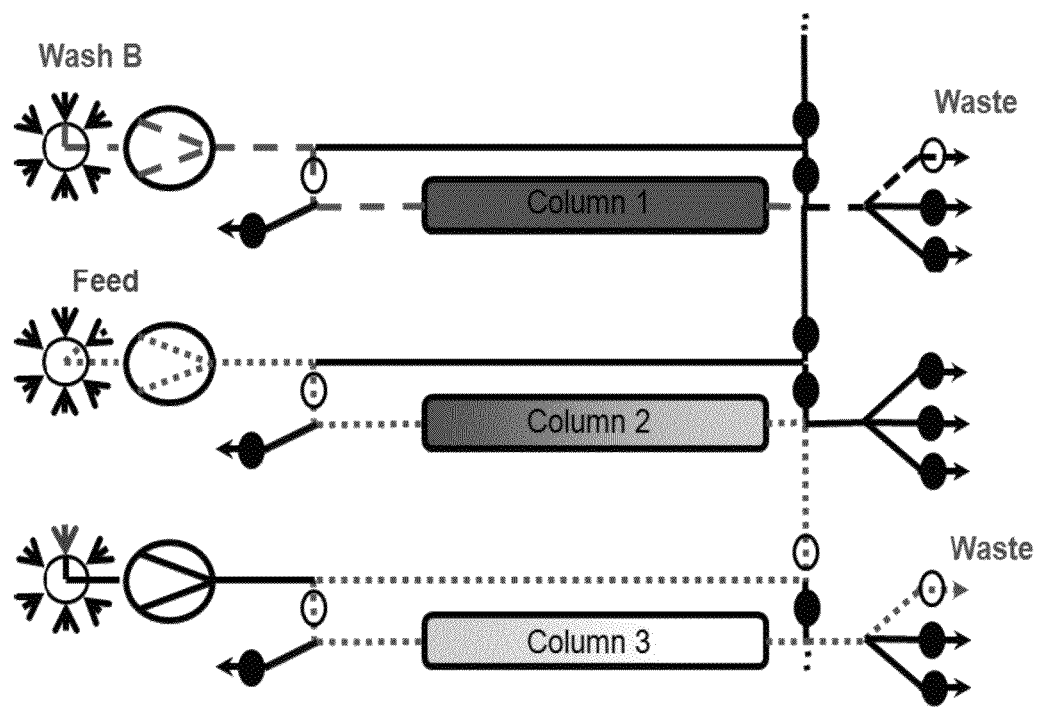
FIG. 7b shows a flow path for a wash of impurities.

In a system with three separation units, typically, at a certain time in the process, one separation unit 1 is fully loaded and needs to be washed, one separation unit 2 is connected to feed to be fully loaded and one separation unit 3 has been eluted and reequilibrated. According to the present invention, at least part of the loading time of separation unit 2, the outlet of separation unit 2 will be in fluid communication with the inlet of separation unit 3 so that unbound target molecule can be bound to separation unit 3. As this fluid connection is typically only necessary during the part of the loading, in the beginning of the loading it is additionally possible to connect the outlet of separation unit 1 with the inlet of separation unit 2 (FIG. 7a). In such case two fluid communications would be possible for the separation unit 2, one containing feedstream, another containing weakly bound or unbound target molecules removed from separation unit 1 during so said washing phase (FIG. 7a). This fluid communication should be maintained during washing of loaded separation unit 1 so that target molecules that might be eluted from separation unit 1 during washing can be captured on separation unit 2. After washing is completed, the fluid communication between separation unit 1 and 2 is stopped. While separation unit 1 undergoes other steps like additional washing (e.g the removal of molecules other then target molecules) (FIG. 7b), CIP, elution, reequilibration, the inlet on separation unit 3 is connected to the outlet of separation unit 2 so that at least in part of the loading time, due to the fluid communication between separation unit 2 and 3, unbound target molecule that is eluted from separation unit 2 can be bound to separation unit 3. It can be easily understood that the same steps are also performed when the feed is shifted to the next separation unit—with the respective separation units.

In a preferred embodiment, the sample that is subjected to the method of the present invention is a clarified sample. That means the sample is subjected to a clarification step prior to loading it onto the separation units for the bind and elute chromatography process according to the present invention.

The clarification step is intended to separate one or more soluble and/or insoluble impurities from the target molecule. For example insoluble impurities like cells and cellular debris are removed from the sample resulting in a clarified fluid containing the target molecule in solution as well as other soluble impurities. A clarification step may involve one or more of the following, either alone or in any combination, centrifugation, settling and/or filtration, preferably tangential flow filtration or depth filtration. Preferably the clarification step does not involve centrifugation but only filtration and/or settling. In a preferred embodiment, filtration is depth filtration.

In some embodiments, depth filters are used to remove one or more insoluble impurities. Depth filters are filters that use a porous filtration medium to retain particles throughout the medium, rather that just on the surface of the medium. A common class of such depth filters are those that comprise a random matrix of fibers bonded (or otherwise fixed), to form a complex, tortuous maze of flow channels. Particle separation in these filters generally results from entrapment by or adsorption to, the fiber matrix. The most frequently used depth filter media for bioprocessing of cell culture broths and other feedstocks usually consists of cellulose fibers, a filter aid such as DE (diatomaceous earth), and a positively charged resin binder.

It has been found that especially good results in the primary removal of particulate impurities can be achieved if the porous depth filter is anisotropic. In some embodiments, the pores have a nominal pore size rating >about 25 µm. In some embodiments, the depth filter comprises at least 2 graded layers of non-woven fibers, wherein the graded layers have a total thickness of about 0.3 cm to about 3 cm.

In some embodiments, depth filters comprise a composite of graded layers of non-woven fibers, cellulose, and diatomaceous earth. The non-woven fibers comprise polypropylene, polyethylene, polyester, nylon or mixtures thereof.

Exemplary depth filters may be found in U.S. Provisional Patent Application No. 61/571,994, incorporated by reference herein.

In some embodiments, a centrifugation and/or tangential flow filtration step may be performed prior to a depth filtration step. Alternatively, a depth filtration step may be performed without the need for a centrifugation and/or a tangential flow filtration step.

In one embodiment, prior to clarification by centrifugation and/or filtration and/or settling, the sample is pretreated with a precipitation composition to precipitate and remove unwanted contaminants from the sample. The precipitation composition at least comprises a precipitant that is able to precipitate contaminants like HCP's, DNA, hormones, etc. from the sample. Precipitants cause the precipitation of a compound from an aqueous and/or soluble state to a non-aqueous and/or insoluble state or aggregate and agglutinate fine particles from a solution, resulting in their settling from the liquid phase and a reduction in solution turbidity.

Examples of suitable precipitants are organic acids (e.g. octanoic acid), inorganic acids (e.g. HCl), other acidic agents that substantially lower the pH towards acidic, salts (e.g., sodium benzoate, sodium chalate, sodium deoxychalate, etc.) other monovalent salts or organic acids which precipitates in the acidic medium). Another example of a precipitant is a short-chain fatty acid such as caprylic acid. In mildly acidic conditions, the addition of short-chain fatty acids such as caprylic acid typically precipitates non IgG proteins while IgG is not precipitated.

Other suitable precipitants are polyelectrolyte polymers (see, e.g., International PCT Patent Application No. WO2008/091740, incorporated by reference herein).

In a preferred embodiment, stimulus responsive polymers are used for precipitating one or more impurities. Examples of such stimulus responsive polymers can be found, e.g., in U.S. Publication Nos., 20080255027, 20090036651, 20090232737 and 20110020327, incorporated by reference herein. Stimulus responsive polymers are generally soluble in an aqueous based solvent under a certain set of process conditions such as pH, temperature and/or salt concentration and are rendered insoluble upon a change in one or more of such conditions and subsequently precipitate out. Exemplary stimulus responsive polymers include, but are not limited to, polyallylamine, polyallylamine modified with a benzyl group or polyvinylamine and polyvinylamine modified with a benzyl group, where the stimulus is phosphate or citrate.

The precipitation composition may further comprise a detergent (TRITON® X-100, TRITON® X-114, NP-40, TWEEN®-20, OTD, SDS, CHAPS, and/or polyethylenegly-cole (PEG) (PEG-1000, PEG 10000) and/or polyvinyl alcohol and/or polyelectrolytes.

The precipitated contaminants are then removed from the sample by clarification prior to loading the sample onto the separation units.

In a preferred embodiment, precipitation is followed by depth filtration, without a centrifugation step to provide the clarified sample.

In a preferred embodiment the clarification of the sample is performed concurrently with the chromatographic purification according to the method of the present invention for at least a part of its duration. In other words, the liquid sample containing the target molecule is not stored in a pool tank after clarification to wait for the whole sample volume to be clarified but as soon as clarified sample is resulting from the clarification process it is continuously used as sample solution for the method of the present invention and loaded on the separation units.

Consequently, the method of the present invention also when using a clarified sample solution does not require the use of pool tanks which are able to store the whole volume of the sample solution. Preferably no pool tanks are used or only pool tanks that can store less than 25% preferably less than 10% of the total volume of the sample solution.

In another embodiment, the target molecule that has been purified with the method according to the present invention is subjected to further process steps like virus inactivation and/or flow through purification.

Viral inactivation renders viruses inactive, or unable to infect, which is important, especially in case the target molecule is intended for therapeutic use.

Many viruses contain lipid or protein coats that can be inactivated by chemical alteration. Rather than simply rendering the virus inactive, some viral inactivation processes are able to denature the virus completely. Methods to inactivate viruses are well known to a person skilled in the art. Some of the more widely used virus inactivation processes include, e.g., use of one or more of the following: solvent/detergent inactivation (e.g. with TRITON® X-100); pasteurization (heating); acidic pH inactivation; and ultraviolet (UV) inactivation. It is possible to combine two or more of these processes; e.g., perform acidic pH inactivation at elevated temperature.

In order to ensure complete and effective virus inactivation, virus inactivation is often performed over an extended period of time with constant agitation to ensure proper mixing of a virus inactivation agent with the sample. For example, in many processes used in the industry today, an output or eluate from a capture step is collected in a pool tank and subjected to virus inactivation over an extended period of time (e.g., >1 to 2 hours, often followed by overnight storage).

The time required for virus inactivation is significantly reduced by performing virus inactivation in-line or by employing a surge tank instead of a pool tank for this step.

In a preferred embodiment, virus inactivation employs use of acidic pH, where the output from the bind and elute chromatography step according to the method of the present invention is subjected to exposure to acidic pH for virus inactivation, either using a surge tank or in-line. The pH used for virus inactivation is typically less than 5.0, or preferably between 3.0 and 4.0. In some embodiments, the pH is about 3.6 or lower. The duration of time used for virus inactivation using an in-line method can be anywhere between 10 minutes or less, 5 minutes or less, 3 minutes or less, 2 minutes or less, or about 1 minute or less. In case of a surge tank, the time required for inactivation is typically less than 1 hour, or preferably less than 30 minutes.

The output from bind and elute chromatography method of the present invention that has been optionally subjected to virus inactivation may then be subjected to flow-through purification.

In a preferred embodiment, the flow-through purification process step employs two or more steps or devices or methods for achieving flow-through purification, which is intended to remove one or more impurities.

In a preferred embodiment the flow through purification process, as described herein, includes one or more of the following steps performed in a flow-through mode: activated carbon; anion exchange chromatography; cation exchange chromatography, mixed-mode chromatography, hydrophobic interaction chromatography, size exclusion, virus filtration or combinations thereof. In some embodiments, one or more, valves, in-line static mixers and/or surge tanks may be used between these steps, in order to change solution conditions.

In a preferred embodiment, flow-through purification employs at least one flow-through anion exchange chromatography (AEX) step, where one or more impurities still remaining in the sample containing the target molecule bind the anion exchange chromatography matrix, whereas the target molecule flows through.

Exemplary anion exchange matrices which may be employed, include, but are not limited to, such as those based on quaternary ammonium ions, as well as weak anion exchangers, such as those based on primary, secondary, and tertiary amine.

The matrices to be used in the flow through purification step can be in the form of particles, membranes, fibrous porous materials or monolithic materials. In case of activated carbon, it can be impregnated into a porous material, e.g., a porous fibrous material. A person skilled in the art knows suitable separation units for holding these matrices, e.g. columns or cartridges. It is also possible to combine two or more different matrices, e.g. a cation exchange matrix and an anion exchange matrix, in one separation unit. The separation units may also be disposable, e.g., MILLISTAK+® Pod.

In a preferred embodiment, the matrices used in the flow through purification step are membrane based matrices, also called membrane adsorbers. The membrane adsorber is preferably a porous membrane sheet made by phase separation methods well known in the art.

In a preferred embodiment, the flow through purification step includes at least an anion exchange step and an activated carbon step. The activated carbon step might be performed prior to anion-exchange chromatography, in combination with anion exchange chromatography or after anion-exchange chromatography, preferably it is performed prior to the anion exchange step. It some embodiments, activated carbon is packed with a cellulose media. Alternatively, activated carbon can be combined with an anion-exchange matrix (e.g., in a column or a cartridge), thereby to further remove one or more impurities from a sample containing a target molecule.

In a preferred embodiment the flow-through purification further includes one or more additional flow-through steps for aggregate removal and/or virus filtration based on size exclusion. In some embodiments, the sample is passed through an adsorptive depth filter, or a charged or modified microporous layer or layers in a normal flow filtration mode of operation, for aggregate removal. In some embodiments, an additional flow-through step employs a cation exchange chromatography (CEX) matrix.

The use of a flow-through cation-exchange step (CEX) may necessitate a reduction of solution pH to increase affinity and capacity for impurities, such as antibody aggregates. Such pH reduction can be performed by a simple in-line addition of suitable solution containing acid, via a three-way valve, a T-style connector, a static mixer, or other suitable devices well known in the art. In addition, a small surge vessel can be employed to provide additional mixing and access for sampling. The volume of the surge vessel, which can be in the form of a bag, a container, or a tank, is usually considerably smaller that the volume of the fluid processed with flow-through setup, for example not more than 10% of the volume of the fluid.

The entire flow-through purification operation (including the anion exchange chromatography step and one or more additional steps, as described herein), are preferably performed continuously without the use of a pool tank between flow-through process steps.

In a preferred embodiment, the flow through step comprises contacting the sample with an activated carbon matrix, an anion exchange matrix, a cation exchange matrix and a size exclusion matrix. Preferably a buffer exchange is performed before passing it through the cation exchange matrix.

If a clarification step is performed prior to the method according to the present invention and/or a flow through purification step is performed after performing the method according to the present invention, in a preferred embodiment, at least the clarification and the bind-and-eltute chromatography step overlap in at least a portion of their duration. Very preferred, the clarification step and the bind-and-elute chromatography step overlap in at least a portion of their duration and the bind-and-elute chromatography step and the flow through purification step overlap in at least a portion of their duration.

In a preferred embodiment, the bind-elute chromatography method according to the present invention as well as all further optional process steps are performed without using tanks for storing the sample solution during the process steps that have more than 25%, preferably not more than 10% of the volume of the sample that was subjected to the process in the beginning.

System

The present invention is also directed to a liquid chromatography system (FIG. 1) for separating at least one target molecule from feed, which system is composed of at least three separation units connected in a circle, each separation unit comprising a chromatography matrix packed in a column. Each separation unit is provided with means for inlet and outlet of liquid. Said means for inlet are at least connected to the solvent delivery system and to the outlet of the previous separation unit in the circle.

Said means of outlet are at least connected to a reservoir or waste and to the inlet of the next separation unit in the circle. In a preferred embodiment, the outlet of each separation unit in the circle is connected with the inlet of each separation unit in the circle so that fluid communication is possible between the outlet of any selected separation unit with the inlet of any other selected separation unit.

In the system according to the present invention, the connecting lines are preferably branched close to each fluid inlet and close to each fluid outlet.

All connecting lines located between the outlet of one separation unit and the inlet of the next separation unit the circle are provided with "on-off" valves for selecting the inlet stream, wherein the inlet stream can be directly connected with a solvent delivery system or is directly connected with the outlet of the previous column. Additionally, all outlets are provided with "on-off" valves to select between the solvent stream directions, wherein the said solvent can be directed towards waste or solvent reservoir or towards the inlet of another separation unit. This setup enables a capture of the leached product from the first capture separation unit (at the end of loading) on the second separation unit (just reequilibrated and ready for capture). This enables to use higher throughputs and binding capacities without the loss of target molecule.

Additionally, the selection of the solvent before the solvent delivery system is done with solvent selection valve with at least two inlets but more like with four and more.

In one embodiment, preferably, the on/off valves are located on the connecting lines in order to stop the flow of the solvent through this line.

Additionally the system can contain just the two solvent delivery system but still be able the perform with the three column methods given above (FIG. 4).

In another embodiment the system according to the present invention might contain of four separation units (FIG. 5a; FIG. 6a)

In another preferred embodiment, the apparatus further comprises one or more detectors. The detectors can be used for control of sample transfer between the columns, for the analysis of sample quality, monitoring etc. The detectors can be located wherever suitable, typically they are located prior to the fluid inlet and/or after the fluid outlet of the separation columns. Examples of suitable detectors are pH detectors, UV detectors, infrared detectors or detectors measuring conductivity.

In another preferred embodiment the apparatus further comprises a computer system. The detectors as well as the pumps and valves are connected to the computer system. This computer system enables control of the pumps and valves and detectors. Preferably, the computer system comprises a software and algorithms that allow the apparatus to be used in a partly or fully automated mode.

In another preferred embodiment, the apparatus comprises a computer system wherein the events (e.g. detector signals) can be used as triggers for the control.

The system may additionally comprise filter units, detection units or other equipment that may be needed or suitable in a chromatographic separation procedure.

The apparatus according to the present invention comprises columns, valves, reservoirs and other equipment that is typically used in chromatography systems. The separation units might for example be stainless steel columns, plastic columns or glass columns that are filled with the respective chromatography matrices and have suitable end-fittings for solvent inlet and outlet.

The apparatus according to the present invention comprises 3 or more, preferably 3, 4 or 5, most preferred 3 separation units having the same chromatography matrix.

The apparatus also comprises at least two buffer reservoirs and at least two pumps, also called the solvent delivery system, which provide for the storage and provision of the buffers needed e.g. for the loading, washing and the elution of the target molecules. Typically all separation units have at least one fluid inlet that is connected to at least one buffer reservoir.

In a very preferred embodiment the apparatus according to the present invention has three separation units and two solvent delivery systems.

In the following the description of the apparatus and the method are focused on an apparatus with three capture separation units having the same chromatography matrix. This is not meant to be restrictive but to make the description more comprehensive. A person skilled in the art can transfer the description also to systems with more than three units as described above.

In other embodiments, the apparatus can comprise additional reservoirs for other buffers, cleaning in place, reequilibration, etc.

Typically the reservoirs and the separation units are connected via connecting lines, valves and pumps. The preferred solvent selection valves for the choice of the solvent prior pump are valves having numerous solvent inlets and 1 solvent outlet which can be connected directly to pump. The amount of the required inlets would correspond to the amount of the used different buffers specifically to individual application. Any pumps which assure solvent flow could be used including peristaltic pumps, isocratic pumps, gradient pumps, high pressure pumps and the like, low pressure pumps and the like. The preferred fluid selection valves for the choice of the fluid introduction prior a system part fluid inlet are valves having numerous fluid inlets and 1 outlet which can be connected to the system part fluid inlet. The preferred fluid selection valves for the choice of the fluid withdraw after the system part fluid outlet are valves having numerous fluid outlets and 1 inlet which can be connected to the system part fluid outlet.

In a preferred embodiment, at least one solvent delivery system is connected to the feedstock reservoir, assuring a constant feedstock stream to the apparatus. This enables a continuous operation in the respect of continuous feed stream. The range of the feed stream might be controlled in order to assure required column binding in the given time range. Usually, for the affinity applications target molecule amount in the feed stream is a decisive criteria for the feed stream.

In another preferred embodiment, the flow rate of the feed is controlled to improve the productivity of each column and more preferably it is kept in the range depending on the target molecule amount in the feed stream.

In another preferred embodiment the flow rate of one or more additional liquid streams are controlled.

Other Issues

In another preferred embodiment, the apparatus further comprises an additional reservoir for cleaning in place. Cleaning in place (CIP) is a technology known to the person skilled in the art. Cleaning in place is the removal of very tightly bound, precipitated or denatured substances from the chromatography matrix. If such contaminants are not removed from the chromatography matrix they might affect the chromatographic properties of the column, decreasing binding capacity and come off in subsequent runs which results in carryover of contaminants or product between cycles. A standard CIP protocols typically includes one to five washes with one to three column volumes of aqueous buffers comprising ingredients like 6 M guanidine hydrochloride
10 mM to 500 mM NaOH
10 mM to 500 mM NaOH and 1 M NaCl,
50 mM NaOH and 1 M $Na_2SO_4$,
150 mM phosphoric acid solution,
6M urea,
20% ethanol,
20% ethanol and 0.5M acetic acid,
20% ethanol and 2M acetic acid,
1% TWEEN® or TRITON® surfactant X-100 or the like.

Concentration of the ingredients like NaOH, the contact time of the CIP buffer on the column as well as the frequency of performing the CIP can be adjusted and determined by the person skilled in the art.

The apparatus according to the present invention preferably has at least one reservoir containing a CIP buffer. The CIP buffer can be used for the CIP of all separation units if suitable. Then the buffer reservoir is in liquid connection with all separation units in a way that the flow of the CIP buffer can be directed to each of the columns independently. Cleaning in place washes can be performed after each separation cycle. Typically CIP is done after every second, third, fourth, fifth, sixth, seventh, eighth, ninth or tenth separation cycle depending on the sample and thus the amount and type of contaminants that might contaminate the separation unit.

In another preferred embodiment, the apparatus comprises an additional reservoir for bound impurity partial or total removal from the adsorbent (wash). Impurity purification, especially removal of HCP and DNA are playing the major role in the biopharmaceutical compound production as host cell DNA levels in biopharmaceutical compounds are regulated by the FDA. It is possible to reduce the number of the bound HCP and DNA levels on the adsorbent through the additional exposure of the loaded adsorbent to various solutions. This technology is known to the person skilled in the art. A standard wash protocols typically includes one to ten washes with one to twenty column volumes of aqueous buffers comprising ingredients like 0.02 M to 2 M NaCl,
0.02 M to 2 M NaCl and $Na_2SO_4$
0.02 M to 2 M $Na_2SO_4$,
0.02 M to 2 M $CaCl_2$
0.02 M to 2 M $MgCl_2$,
0.02 M to 2 M $MgSO_4$,
10-20% organic solvents,
10-20% polyethylene glycol and polypropylene glycol,
0.5M amino acids such as arginine and glycine,
0.1-1% TWEEN® or TRITON® surfactant X-100 or the like.

Concentration of the ingredients like NaCl, the contact time of the wash buffer on the column, the buffer pH value as well as the frequency of performing the wash can be adjusted and determined by the person skilled in the art.

In another preferred embodiment the washing steps are carried out with different buffers.

In another preferred embodiment each adsorbent is washed by multiple washing steps.

In one embodiment, the system comprises three or more separation units with an affinity chromatography matrix. Suitable affinity matrices are matrices having Protein A, Protein G, Protein L or Protein or functional groups (e.g. PROSEP® Highcap (Merck Millipore), PROSEP® Ultra Plus (Merck Millipore), POROS® Prot A(Life Technologies), A650F (Tosoh), MABSELECT® Sure (GE).

The affinity chromatography matrix to be used in the apparatus according to the present invention comprises particles with average diameters between 40 and 200 µm, preferred diameters and pore sizes have been given above when describing the method according to the present invention.

The particles can be regularly or irregularly formed. They can be made of any material suitable as chromatographic sorbent, like polysaccharides (such as agarose and cellulose); and other mechanically stable matrices such as silica (e.g. controlled pore glass), poly(styrenedivinyl)benzene, polyacrylamide, polymthqacrylates, ceramic particles or copolymers of hydrophilically substituted alkyl vinyl ethers like 1,2-ethanediol monovinyl ether, 1,3-propanediol monovinyl ether, 1,4-butanediol monovinyl ether, 1,5-pentanediol monovinyl ether, 1,6-hexanediol monovinyl ether, diethylene glycol monovinyl ether or cyclohexanedimethanol monovinyl ether and crosslinking agents like divinylethyleneurea (1,3-divinylimidazolin-2-one) or divinylpropyleneurea (1,3-divinyltetrahydropyrimidin-2-one) and derivatives of any of the above. Examples of copolymers of hydrophilically substituted alkyl vinyl ethers are disclosed in EP 1910433. Preferred are materials which show a high rigidity so that velocities above 1000 cm/h can be applied.

In other preferred embodiment, the described apparatus can be connected to a bioreactor, perfusion bioreactor and/or purification methodology applied for the partial impurity removal (like cell debris, etc.), like depth filters, centrifugation, clarification, sedimentation, fluctuation technologies that assures a constant feed stream. This is not only essential for the method requirement for a need of continuous feed stream, but would provide shorter processing time and maintained product quality (like lower levels of aggregation, etc.) while avoiding long storage times between the target molecule production and/or feed stream purification and target molecule capture.

In another preferred embodiment, the product outlet stream can be directly connected to other purification techniques, such as ion exchange chromatography, mixed mode chromatography, reversed phase chromatography, HIC chromatography, SEC chromatography modes, depth filtration, sedimentation, fluctuation technologies, etc. or gathered in the reservoir, surge bag, storage bag.

In another preferred experiment, the product outlet stream is connected to a reservoir, where at least one elution pool from a single adsorbent fits, wherein a continuous or semi-continuous withdraw of the pooled solution can be performed, enabling a direct connection to the following purification technologies. This would assure not only more constant conditions (in comparison to standard chromatography elution profile) for the following purification technologies in respect to target concentration, pH and conductivity values, but would assure faster processing since smaller processed target molecule amounts can be directly purified with further technologies in order to enable shorter total purification process.

In another preferred embodiment an appropriate column diameter and length has to be chosen to assure an optimum operation. More preferably the adsorbent bed height should be shorter then 10 cm and even more preferably 4-6 cm height. This influences the pressure drop on the column that in the industrial scale application is not to exceed 3 bars. The advantage is the operation at 1000 cm/h and greater without exceeding pressure limitations.

The entire disclosures of all applications, patents, and publications cited above and below and of corresponding EP application EP 12002828.7, filed Apr. 23, 2012 and of corresponding U.S. provisional application 61/666,453 filed Jun. 29, 2012 are hereby incorporated by reference.

EXAMPLES

Example I

Continuous Purification of mAb-x (1 mg/ml) on PUP for >100 Cycles with Corresponding Data The monoclonal antibody mAb-x in cell culture (SP 2/0) solution, which had 1 mg/ml monoclonal antibody composing a fraction of 21% of all components in the solution (according to analytical SEC), where HCP amount was 600000 ng/mg antibody (according to immunoenzymetric assay SP 2/0), was purified on the ProtA resin (PUP) under the following conditions. Chromatography columns: PUP resin was packed in a 16×55 mm column; the column was then equilibrated with 25 mM PBS buffer pH 7.2 at 33.3 ml/min. In total three columns were packed. To prepare the sample: monoclonal antibody cell culture solution was filtered through a 0.45 μm filter. The solution conductivity was at about 16 mS/cm and pH6.4. All three columns were attached to a continuous chromatographic system, enabling a connection between the first column and the second column, as well as a connection between the second column and the third column and a connection between the third column and the first column. The whole experiment is divided in three steps. As the first step is started first column is connected with the second column. This column group is loaded with the prepared sample at 1500 cm/h, while the third column is washed at 1500 cm/h for at least 3 CV with 25 mM TRIS and 1.5 M NaCl buffer pH 7, then washed at 1500 cm/h for at least 3 CV with 25 mM TRIS buffer pH 7.2, then eluted at 1500 cm/h with 50 mM glycine buffer pH 2.7, following by column cleaning at 1500 cm/h with 150 mM phosphoric acid, following by reequilibration at 1500 cm/h with 25 mM TRIS buffer pH7.2.

As the second step is started the second column is connected with the third column. This column group is loaded with the prepared sample at 1500 cm/h, while the first column is washed at 1500 cm/h for at least 3 CV with 25 mM TRIS and 1.5 M NaCl buffer pH 7, then washed at 1500 cm/h for at least 3 CV with 25 mM TRIS buffer pH 7.2, then eluted at 1500 cm/h with 50 mM glycine buffer pH 2.7, following by column cleaning at 1500 cm/h with 150 mM phosphoric acid, following by reequilibration at 1500 cm/h with 25 mM TRIS buffer pH7.2.

As the third step is started the third column is connected with the first column. This column group is loaded with the prepared sample at 1500 cm/h, while the second column is washed at 1500 cm/h for at least 3 CV with 25 mM TRIS and 1.5 M NaCl buffer pH 7, then washed at 1500 cm/h for at least 3 CV with 25 mM TRIS buffer pH 7.2, then eluted at 1500 cm/h with 50 mM glycine buffer pH 2.7, following by column cleaning at 1500 cm/h with 150 mM phosphoric acid, following by reequilibration at 1500 cm/h with 25 mM TRIS buffer pH7.2.

Figure 9:
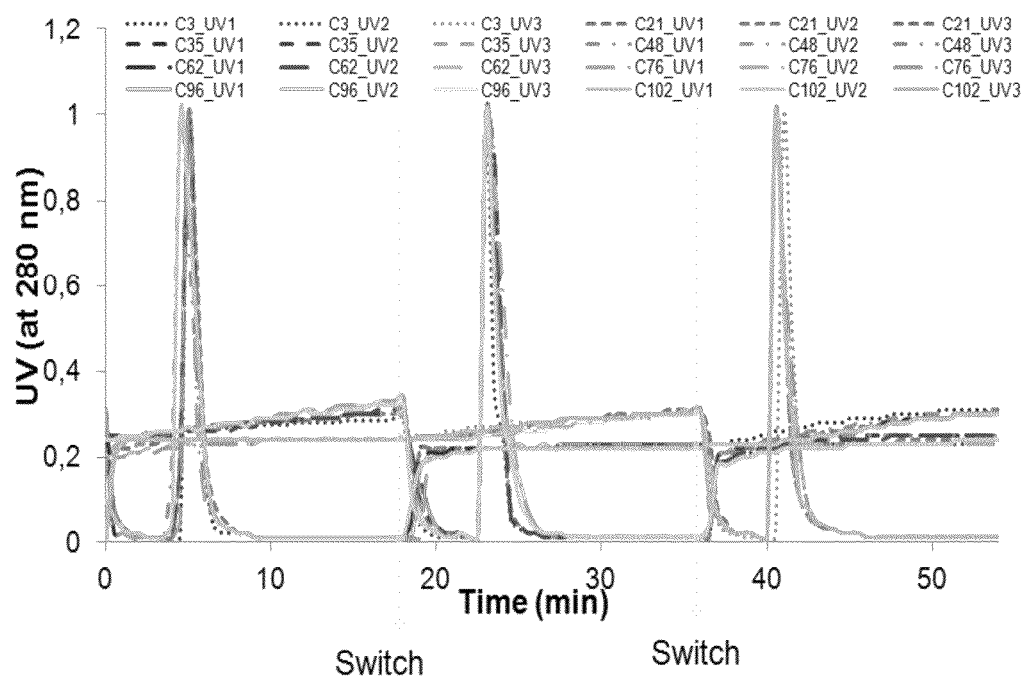
FIG. 9 shows an overlay of the UV signal traces for a 103 cycle run on three separation unit continuous chromatography system in mAbA purification experiment applying PROSEP®-vA Ultra Plus columns.

The named steps were repeated at least 100 times and the steady state operation was obtained in the second cycle. The UV signal traces are given in FIG. 9, showing all process step UV traces that each column is going through in each single cycle. Starting with a wash of loaded first column simultaneously loading the next column in the series coupled with after the next column in the series. As still the named columns are being loaded the previously loaded column is eluted (first peak) CIPed and reequilibrated. At the $18^{th}$ minute the loading of the next column is done and the load is switched onto the column after the next in the series followed by the first column, consequently proceeding with the necessary process for the next column including wash, elution (second peak), CIP and reequilibration. At the same time after the next and first columns are being loaded. At the 36th minute the loading of the after the next column is done and the load is switched to the first column followed by the next column, consequently proceeding with the necessary process for the after the next column including wash, elution (third peak), CIP and reequilibration.

Figure 10:
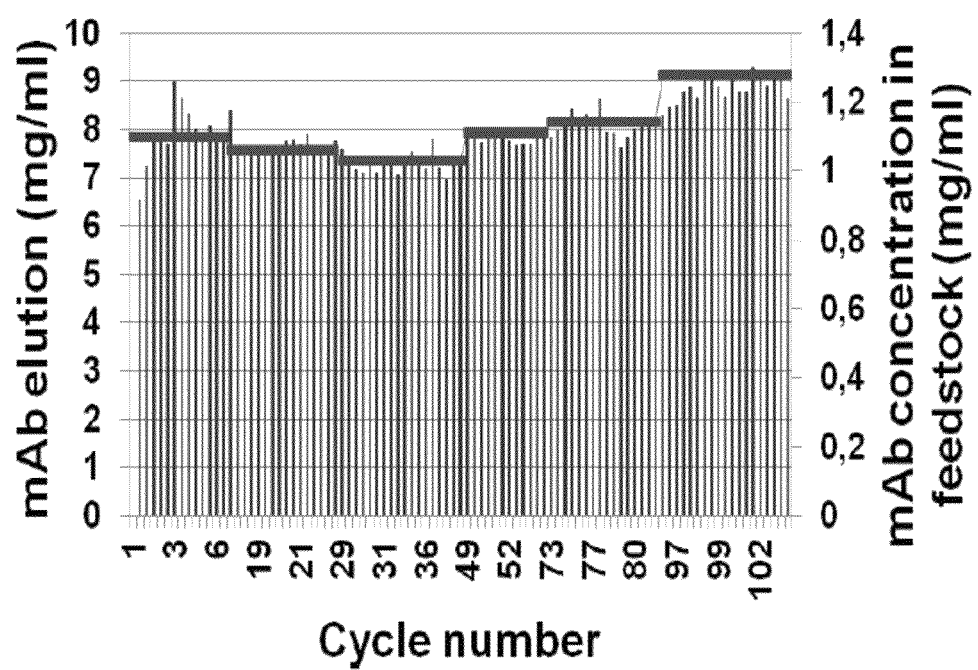
FIG. 10 shows an mAbA input concentrations and mAb elution concentrations for a 103 cycle run on three separation unit continuous chromatography system applying PROSEP®-vA Ultra Plus columns.
Figure 11:
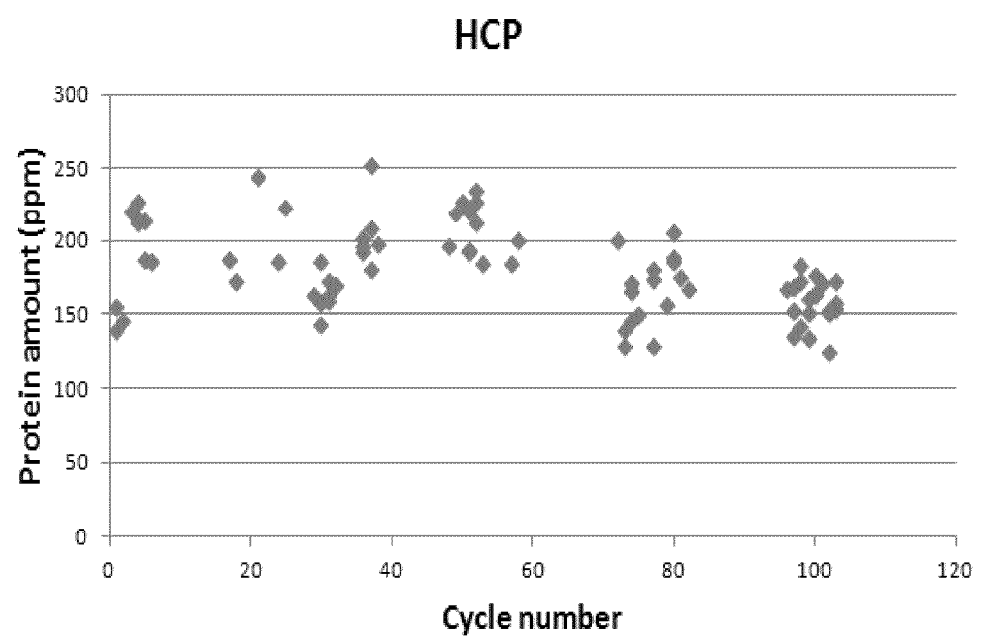
FIG. 11 shows HCP concentration in the elution pools for a 103 cycle run on three separation unit continuous chromatography system applying PROSEP®-vA Ultra Plus columns for the purification of mAbA.
Figure 12:
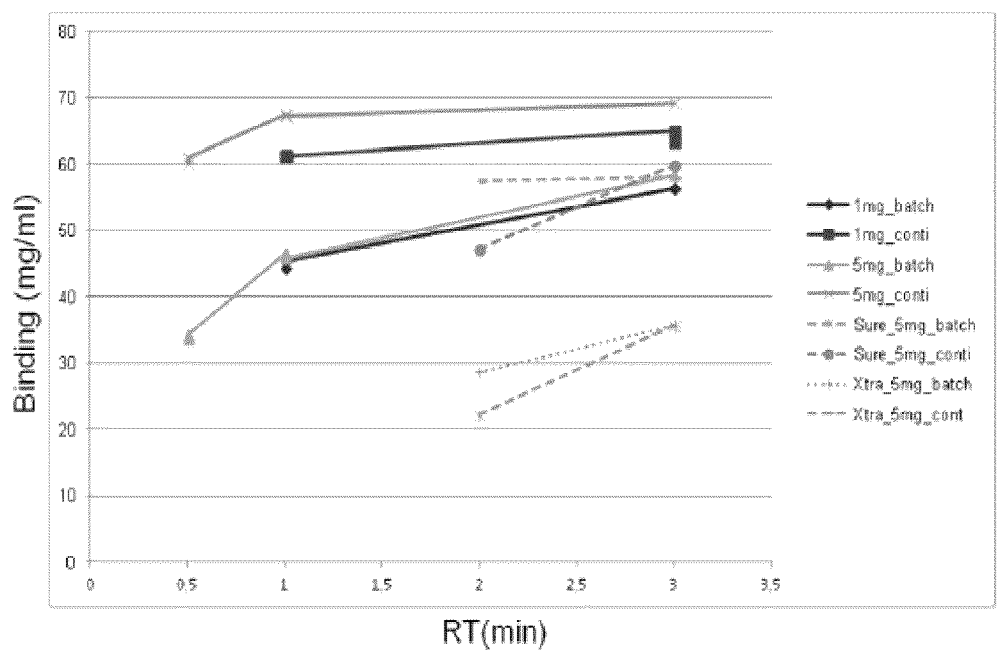
FIG. 12 shows dynamic binding capacity for various ProtA resins and various mAb concentrations in batch and continuous operation modes. Note the legend where material is not given refers to the PUP material. All columns had the same dimensions of 0.8*10 cm.

The eluted fractions contained 7-9 mg/ml antibody (see FIG. 10) resulting in >35 mg/ml packed bed binding capacity and <5% target molecule loss and the average productivity of 50 g/ml/h (compared to batch operation the productivity was 9.6 g/ml/h), that composed 99.9% of all components (according to analytical SEC), where HCP amount was 120-250 ppm (according to immunoenzymetric assay SP 2/0) (see FIG. 11). The amount of the leached ProtA remained stable throughout all experiment resulting in the values between 10-60 ppm.

Example II

Figure 8:
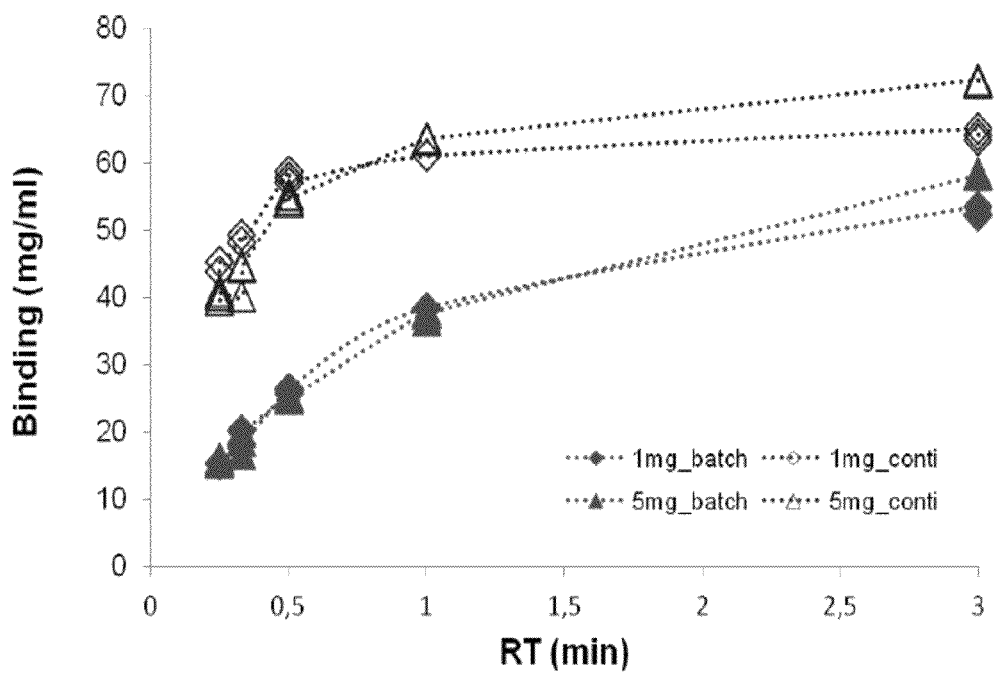
FIG. 8 shows a compelling advantage of continuous chromatography over the standard batch methods, expressed in binding capacity over residence time for the PROSEP®-vA Ultra Plus resin.

Following examples were done to explore the potential difference in the binding capacity value dependency on the residence time for the batch and for the described continuous chromatography method. As indicated in FIG. 8, the binding capacity values measured till 1% brake through values for the standard batch operation were decreasing with decreasing residence values resulting in <20 mg/ml binding capacities for <0.45 min residence time. In contrast the binding capacity values for a continuous chromatography methods remained >35 mg/ml in the measured range of >0.2 min residence time. The current example was done on pure mAb-x example and at different initial titers (1 mg/ml and 5 mg/ml).

Based on these results feedstock examples are given below:
a) Continuous Purification of mAb-y (0.5 mg/ml) on PUP The monoclonal antibody mAb-y in cell culture (CHO) solution, which had 0.5 mg/ml monoclonal antibody composing a fraction of 9% of all components in the solution (according to analytical SEC), where HCP amount was 250000 ng/mg antibody (according to immunoenzymetric assay CHO), was purified on the ProtA resin (PUP) under the following conditions. Chromatography columns: PUP resin was packed in a 16×55 mm column; the column was then equilibrated with 25 mM PBS buffer pH 7.2 at 33.3 ml/min. In total three columns were packed. To prepare the sample: monoclonal antibody cell culture solution was filtered through a 0.45 μm filter. The solution conductivity was at about 14 mS/cm and pH6.8. All three columns were attached to a continuous chromatographic system, enabling a connection between the first column and the second column, as well as a connection between the second column and the third column and a connection between the third column and the first column. The whole experiment is divided in three steps. As the first step is started first column is connected with the second column. This column group is loaded with the prepared sample at 1500 cm/h, while the third column is washed at 1500 cm/h for at least 5 CV with 25 mM TRIS and 0.05 M NaCl buffer pH 7, then washed at 1500 cm/h for at least 3 CV with 25 mM TRIS buffer pH 7.2, then eluted at 1500 cm/h with 50 mM glycine buffer pH 2.8, following by column cleaning at 1500 cm/h with 150 mM phosphoric acid, following by reequilibration at 1500 cm/h with 25 mM TRIS buffer pH7.0.

As the second step is started the second column is connected with the third column. This column group is loaded with the prepared sample at 1500 cm/h, while the first column is washed at 1500 cm/h for at least 5 CV with 25 mM TRIS and 0.05 M NaCl buffer pH 7, then washed at 1500 cm/h for at least 3 CV with 25 mM TRIS buffer pH 7.2, then eluted at 1500 cm/h with 50 mM glycine buffer pH 2.8, following by column cleaning at 1500 cm/h with 150 mM phosphoric acid, following by reequilibration at 1500 cm/h with 25 mM TRIS buffer pH7.2.

As the third step is started the third column is connected with the first column. This column group is loaded with the prepared sample at 1500 cm/h, while the second column is washed at 1500 cm/h for at least 5 CV with 25 mM TRIS and 0.05 M NaCl buffer pH 7, then washed at 1500 cm/h for at least 3 CV with 25 mM TRIS buffer pH 7.2, then eluted at 1500 cm/h with 50 mM glycine buffer pH 2.8, following by column cleaning at 1500 cm/h with 150 mM phosphoric acid, following by reequilibration at 1500 cm/h with 25 mM TRIS buffer pH7.2.

The named steps were repeated at least twice.

The eluted fractions resulted in >37 mg/ml packed bed binding capacity and <5% target molecule loss and the average productivity of 136.12 g/ml/h (compared to batch operation the productivity was 7.12 g/ml/h), that composed 99.9% of all components (according to analytical SEC), where the average HCP amount was 1300 ppm (according to immunoenzymetric assay CHO).

|  | RT (min) | Velocity (cm/h) | Recovery (%) | BC (mg/ml) | Productivity (g/L/h) | Purity (ppm) |
|---|---|---|---|---|---|---|
| Batch slow | 4 | 83 | 95 | 38.7 | 7.12 | 1251 |
| Bach fast | 0.22 | 1500 | 95 | 7.01 | 19.4 | 1198 |
| Conti 3 columns | 0.22 | 1500 | 95 | 37.1 | 136.12 | 1300 |

The experimental conditions were compared to two individual batch cases, where the standard conditions of batch purification were applied using 4 minutes residence time for the loading and washing, elution, CIP and reequilibration conditions identical to the ones given above. And to the second case where the loading of a standard batch operation was performed at 0.22 minutes residence time. The obtained productivity in this case was 19.4 g/ml/h.

b) Continuous Purification of mAb-z (1 mg/ml) on PUP

The monoclonal antibody mAb-z in cell culture (CHO-DG44) solution, which had 1 mg/ml monoclonal antibody composing a fraction of 14% of all components in the solution (according to analytical SEC), where HCP amount was 200000 ng/mg antibody (according to immunoenzymetric assay CHO), was purified on the ProtA resin (PUP) under the following conditions. Chromatography columns: PUP resin was packed in a 16×55 mm column; the column was then equilibrated with 25 mM PBS buffer pH 7.2 at 33.3 ml/min. In total three columns were packed. To prepare the sample: monoclonal antibody cell culture solution was filtered through a 0.45 μm filter. The solution conductivity was at about 13 mS/cm and pH6.2. All three columns were attached to a continuous chromatographic system, enabling a connection between the first column and the second column, as well as a connection between the second column and the third column and a connection between the third column and the first column. The whole experiment is divided in three steps. As the first step is started first column is connected with the second column. This column group is loaded with the prepared sample at 1500 cm/h, while the third column is washed at 1500 cm/h for at least 5 CV with 25 mM TRIS and 0.05 M NaCl buffer pH 7, then washed at 1500 cm/h for at least 3 CV with 25 mM TRIS buffer pH 7.2, then eluted at 1500 cm/h with 50 mM glycine buffer pH 2.8, following by column cleaning at 1500 cm/h with 150 mM phosphoric acid, following by reequilibration at 1500 cm/h with 25 mM TRIS buffer pH7.0.

As the second step is started the second column is connected with the third column. This column group is loaded with the prepared sample at 1500 cm/h, while the first column is washed at 1500 cm/h for at least 5 CV with 25 mM TRIS and 0.05 M NaCl buffer pH 7, then washed at 1500 cm/h for at least 3 CV with 25 mM TRIS buffer pH 7.2, then eluted at 1500 cm/h with 50 mM glycine buffer pH 2.8, following by column cleaning at 1500 cm/h with 150 mM phosphoric acid, following by reequilibration at 1500 cm/h with 25 mM TRIS buffer pH7.2.

As the third step is started the third column is connected with the first column. This column group is loaded with the prepared sample at 1500 cm/h, while the second column is washed at 1500 cm/h for at least 5 CV with 25 mM TRIS and 0.05 M NaCl buffer pH 7, then washed at 1500 cm/h for at least 3 CV with 25 mM TRIS buffer pH 7.2, then eluted at 1500 cm/h with 50 mM glycine buffer pH 2.8, following by column cleaning at 1500 cm/h with 150 mM phosphoric acid, following by reequilibration at 1500 cm/h with 25 mM TRIS buffer pH7.2.

The named steps were repeated at least twice.

The eluted fractions resulted in >37 mg/ml packed bed binding capacity and <5% target molecule loss and the average productivity of 271.4 g/ml/h (compared to batch operation the productivity was 14.27 g/ml/h), that composed 99.9% of all components (according to analytical SEC), where the average HCP amount was 1551 ppm (according to immunoenzymetric assay CHO).

|  | RT (min) | Velocity (cm/h) | Recovery (%) | BC (mg/ml) | Productivity (g/L/h) | Purity (ppm) |
| --- | --- | --- | --- | --- | --- | --- |
| Batch slow | 4 | 83 | 95 | 38.7 | 14.27 | 1500 |
| Batch fast | 0.22 | 1500 | 95 | 7.01 | 45.13 | 1487 |
| Conti 3 columns | 0.22 | 1500 | 96 | 37.1 | 271.4 | 1551 |

The experimental conditions were compared to two individual batch cases, where the standard conditions of batch purification were applied using 4 minutes residence time for the loading and washing, elution, CIP and reequilibration conditions identical to the ones given above. And to the second case where the loading of a standard batch operation was performed at 0.22 minutes residence time. The obtained productivity in this case was 45.13 g/ml/h.

c) Continuous Purification of mAb-w (2.4 mg/ml) on PUP

The monoclonal antibody mAb-z in cell culture (NH0) solution, which had 2.4 mg/ml monoclonal antibody composing a fraction of 35% of all components in the solution (according to analytical SEC), where HCP amount was 350000 ng/mg antibody (according to immunoenzymetric assay NH0), was purified on the ProtA resin (PUP) under the following conditions. Chromatography columns: PUP resin was packed in a 16×55 mm column; the column was then equilibrated with 25 mM PBS buffer pH 7.2 at 33.3 ml/min. In total three columns were packed. To prepare the sample: monoclonal antibody cell culture solution was filtered through a 0.45 μm filter. The solution conductivity was at about 17 mS/cm and pH5.8. All three columns were attached to a continuous chromatographic system, enabling a connection between the first column and the second column, as well as a connection between the second column and the third column and a connection between the third column and the first column. The whole experiment is divided in three steps. As the first step is started first column is connected with the second column. This column group is loaded with the prepared sample at 1032 cm/h, while the third column is washed at 1500 cm/h for at least 5 CV with 25 mM TRIS and 0.05 M NaCl buffer pH 7, then washed at 1500 cm/h for at least 3 CV with 25 mM TRIS buffer pH 7.2, then eluted at 1500 cm/h with 50 mM glycine buffer pH 2.8, following by column cleaning at 1500 cm/h with 150 mM phosphoric acid, following by reequilibration at 1500 cm/h with 25 mM TRIS buffer pH7.0.

As the second step is started the second column is connected with the third column. This column group is loaded with the prepared sample at 1032 cm/h, while the first column is washed at 1500 cm/h for at least 5 CV with 25 mM TRIS and 0.05 M NaCl buffer pH 7, then washed at 1500 cm/h for at least 3 CV with 25 mM TRIS buffer pH 7.2, then eluted at 1500 cm/h with 50 mM glycine buffer pH 2.8, following by column cleaning at 1500 cm/h with 150 mM phosphoric acid, following by reequilibration at 1500 cm/h with 25 mM TRIS buffer pH7.2.

As the third step is started the third column is connected with the first column. This column group is loaded with the prepared sample at 1032 cm/h, while the second column is washed at 1500 cm/h for at least 5 CV with 25 mM TRIS and 0.05 M NaCl buffer pH 7, then washed at 1500 cm/h for at least 3 CV with 25 mM TRIS buffer pH 7.2, then eluted at 1500 cm/h with 50 mM glycine buffer pH 2.8, following by column cleaning at 1500 cm/h with 150 mM phosphoric acid, following by reequilibration at 1500 cm/h with 25 mM TRIS buffer pH7.2.

The named steps were repeated at least twice.

The eluted fractions resulted in >30 mg/ml packed bed binding capacity and <5% target molecule loss and the average productivity of 407.24 g/ml/h (compared to batch operation the productivity was 34.97 g/ml/h), that composed 99.9% of all components (according to analytical SEC), where the average HCP amount was 900 ppm (according to immunoenzymetric assay NH0).

|  | RT (min) | Velocity (cm/h) | Recovery (%) | BC (mg/ml) | Productivity (g/L/h) | Purity (ppm) |
| --- | --- | --- | --- | --- | --- | --- |
| Batch slow | 4 | 83 | 95 | 38.7 | 34.97 | 700 |
| Batch fast | 0.32 | 1032 | 95 | 9.6 | 101.95 | 1200 |
| Conti 3 columns | 0.32 | 1032 | 95 | 30 | 407.24 | 900 |

The experimental conditions were compared to two individual batch cases, where the standard conditions of batch purification were applied using 4 minutes residence time for the loading and washing, elution, CIP and reequilibration conditions identical to the ones given above. And to the second case where the loading of a standard batch operation was performed at 0.32 minutes residence time. The obtained productivity in this case was 101.95 g/ml/h.

d) Continuous Purification of mAb-x (3.5 mg/ml) on PUP

The monoclonal antibody mAb-x in cell culture (SP2/0) solution, which had 3.5 mg/ml monoclonal antibody composing a fraction of 45% of all components in the solution (according to analytical SEC), where HCP amount was 450000 ng/mg antibody (according to immunoenzymetric assay SP2/0), was purified on the ProtA resin (PUP) under the following conditions. Chromatography columns: PUP resin was packed in a 16×55 mm column; the column was then equilibrated with 25 mM PBS buffer pH 7.2 at 33.3 ml/min. In total three columns were packed. To prepare the sample: monoclonal antibody cell culture solution was filtered through a 0.45 μm filter. The solution conductivity was at about 17 mS/cm and pH5.8. All three columns were attached to a continuous chromatographic system, enabling a connection between the first column and the second column, as well as a connection between the second column and the third column and a connection between the third column and the first column. The whole experiment is divided in three steps. As the first step is started first column is connected with the second column. This column group is loaded with the prepared sample at 920 cm/h, while the third column is washed at 1500 cm/h for at least 5 CV with 25 mM TRIS and 0.05 M NaCl buffer pH 7, then washed at 1500 cm/h for at least 3 CV with 25 mM TRIS buffer pH 7.2, then eluted at 1500 cm/h with 50 mM glycine buffer pH 2.8, following by column cleaning at 1500 cm/h with 150 mM phosphoric acid, following by reequilibration at 1500 cm/h with 25 mM TRIS buffer pH7.0.

As the second step is started the second column is connected with the third column. This column group is loaded with the prepared sample at 920 cm/h, while the first column is washed at 1500 cm/h for at least 5 CV with 25 mM TRIS and 0.05 M NaCl buffer pH 7, then washed at 1500 cm/h for at least 3 CV with 25 mM TRIS buffer pH 7.2, then eluted at 1500 cm/h with 50 mM glycine buffer pH 2.8, following by column cleaning at 1500 cm/h with 150 mM phosphoric acid, following by reequilibration at 1500 cm/h with 25 mM TRIS buffer pH7.2.

As the third step is started the third column is connected with the first column. This column group is loaded with the prepared sample at 920 cm/h, while the second column is washed at 1500 cm/h for at least 5 CV with 25 mM TRIS and 0.05 M NaCl buffer pH 7, then washed at 1500 cm/h for at least 3 CV with 25 mM TRIS buffer pH 7.2, then eluted at 1500 cm/h with 50 mM glycine buffer pH 2.8, following by column cleaning at 1500 cm/h with 150 mM phosphoric acid, following by reequilibration at 1500 cm/h with 25 mM TRIS buffer pH7.2.

The named steps were repeated at least twice.

The eluted fractions resulted in >57.1 mg/ml packed bed binding capacity and <5% target molecule loss in the loading and ~5% target molecule loss in the elution resulting in 90% product recovery and the average productivity of 572 g/ml/h (compared to batch operation the productivity was 46.19 g/ml/h), that composed 99.9% of all components (according to analytical SEC), where the average HCP amount was 2100 ppm (according to immunoenzymetric assay SP2/0).

|  | RT (min) | Velocity (cm/h) | Recovery (%) | BC (mg/ml) | Productivity (g/L/h) | Purity (ppm) |
|---|---|---|---|---|---|---|
| Batch slow | 4 | 83 | 95 | 38.7 | 46.19 | 1800 |
| Batch fast | 0.36 | 920 | 90 | 9.6 | 88.7 | 1700 |
| Conti 3 columns | 0.36 | 920 | 90 | 57.2 | 572 | 2100 |

The experimental conditions were compared to two individual batch cases, where the standard conditions of batch purification were applied using 4 minutes residence time for the loading and washing, elution, CIP and reequilibration conditions identical to the ones given above. And to the second case where the loading of a standard batch operation was performed at 0.36 minutes residence time. The obtained productivity in this case was 88.7 g/ml/h.

Example III

Other materials can be used in the application as well, such as MABSELECT SURE®, though it must be taken into account, that the operational conditions are not the same as the shown above for the PUP material. Just as an example MABSELECT SURE® usually is applied at 500 cm/h and MABSELECT XTRA® at 300 cm/h. Please see the FIG. below displaying the difference in the achievable binding capacity for the operation in the batch and in our continuous approach for three different materials (PUP, MABSELECT XTRA®, MABSELECT SURE®) and two different mAb titers (1 mg and 5 mg/ml).

The monoclonal antibody mAb-x in cell culture (SP2/0) solution, which had 0.68 mg/ml monoclonal antibody composing a fraction of 10% of all components in the solution (according to analytical SEC), where HCP amount was 450000 ng/mg antibody (according to immunoenzymetric assay SP2/0), was purified on the ProtA resin (MABSELECT SURE®) under the following conditions. Chromatography columns: MABSELECT SURE® resin was packed in a 10×60 mm column; the column was then equilibrated with 25 mM PBS buffer pH 7.2 at 20 ml/min. In total three columns were packed. To prepare the sample: monoclonal antibody cell culture solution was filtered through a 0.45 μm filter. The solution conductivity was at about 16 mS/cm and pH6.8. All three columns were attached to a continuous chromatographic system, enabling a connection between the first column and the second column, as well as a connection between the second column and the third column and a connection between the third column and the first column. The whole experiment is divided in three steps. As the first step is started first column is connected with the second column. This column group is loaded with the prepared sample at 917.2 cm/h, while the third column is washed at 1000 cm/h for at least 5 CV with 50 mM acetate and 1.5 M NaCl buffer pH 6.8, then washed at 1000 cm/h for at least 3 CV with 50 mM acetate buffer pH 6.8, then eluted with 20 mM acetic acid buffer pH 3.2, following by column cleaning at with 50 mM sodium hydroxyde, following by reequilibration with 50 mM acetate buffer pH6.8.

As the second step is started the second column is connected with the third column. This column group is loaded with the prepared sample at 917.2 cm/h, while the first column is washed at 1000 cm/h for at least 5 CV with 50 mM acetate and 1.5 M NaCl buffer pH 6.8, then washed at 1000 cm/h for at least 3 CV with 50 mM acetate buffer pH 6.8, then eluted with 20 mM acetic acid buffer pH 3.2, following by column cleaning at with 50 mM sodium hydroxyde, following by reequilibration with 50 mM acetate buffer pH6.8.

As the third step is started the third column is connected with the first column. This column group is loaded with the prepared sample at 917.2 cm/h, while the second column is washed at 1000 cm/h for at least 5 CV with 50 mM acetate and 1.5 M NaCl buffer pH 6.8, then washed at 1000 cm/h for at least 3 CV with 50 mM acetate buffer pH 6.8, then eluted with 20 mM acetic acid buffer pH 3.2, following by column cleaning at with 50 mM sodium hydroxyde, following by reequilibration with 50 mM acetate buffer pH6.8.

The named steps were repeated at least twice.

The eluted fractions resulted in >38 mg/ml packed bed binding capacity and <5% target molecule loss in the loading and ~2% target molecule loss in the elution resulting in 93% product recovery and the average productivity of 102 g/ml/h (compared to batch operation the productivity was 12.1 g/ml/h), that composed 99.9% of all components (according to analytical SEC), where HCP amount was in between 120-150 ppm (according to immunoenzymetric assay SP2/0).

|  | RT (min) | Velocity (cm/h) | Recovery (%) | BC (mg/ml) | Productivity (g/L/h) | Purity (ppm) |
|---|---|---|---|---|---|---|
| Batch slow | 3 | 122 | 95 | 35.5 | 12.1 | 133 |
| Conti 3 columns | 0.39 | 917.2 | 93 | 38.38 | 102.34 | 120-150 |

Example IV

Figure 13:
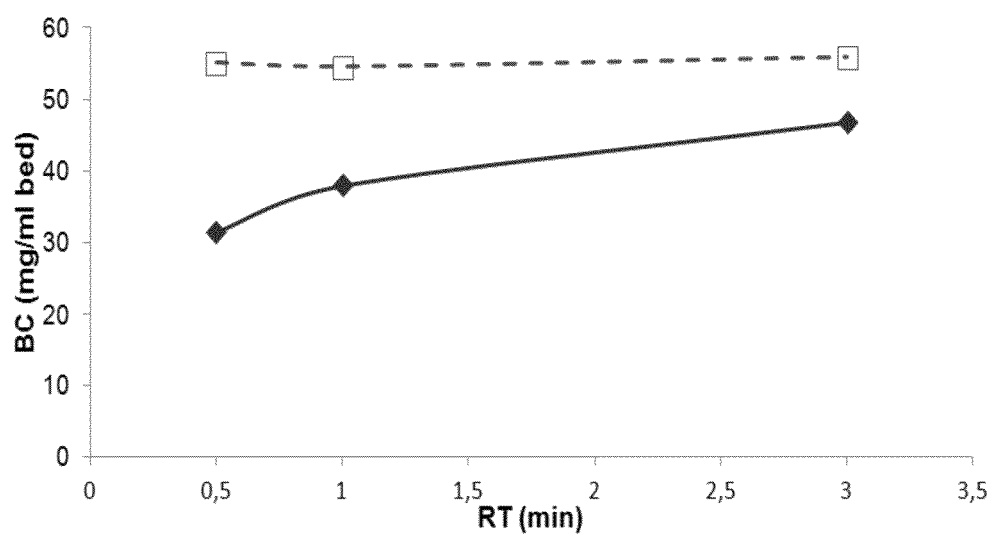
FIG. 13 shows a compelling advantage of continuous chromatography over the standard batch methods, expressed in binding capacity over residence time for the ESHMUNO® S resin.
Figure 14:
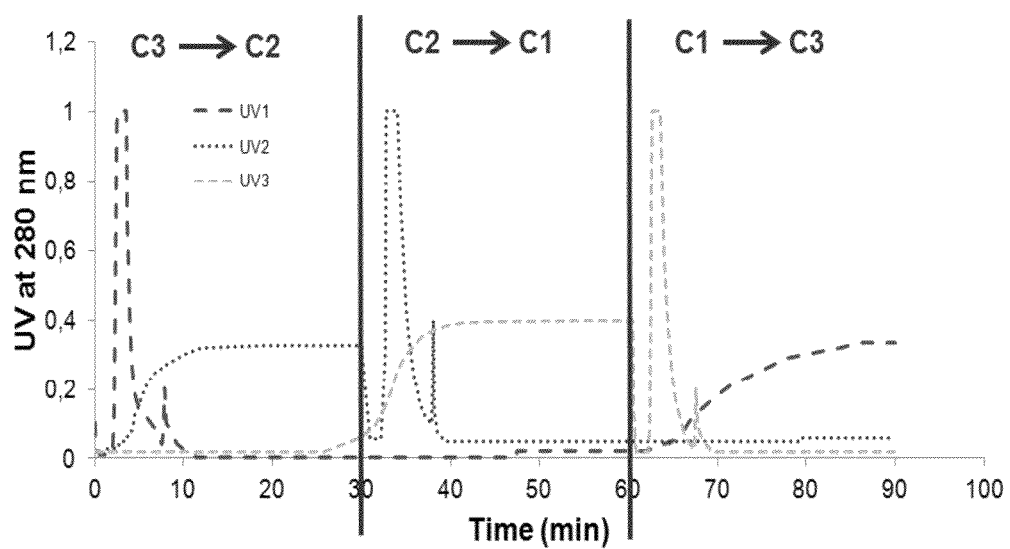
FIG. 14 shows an overlay of the UV signal traces for a run on three separation unit continuous chromatography system in mAbA purification experiment applying ESHMUNO® S columns.
Figure 15:
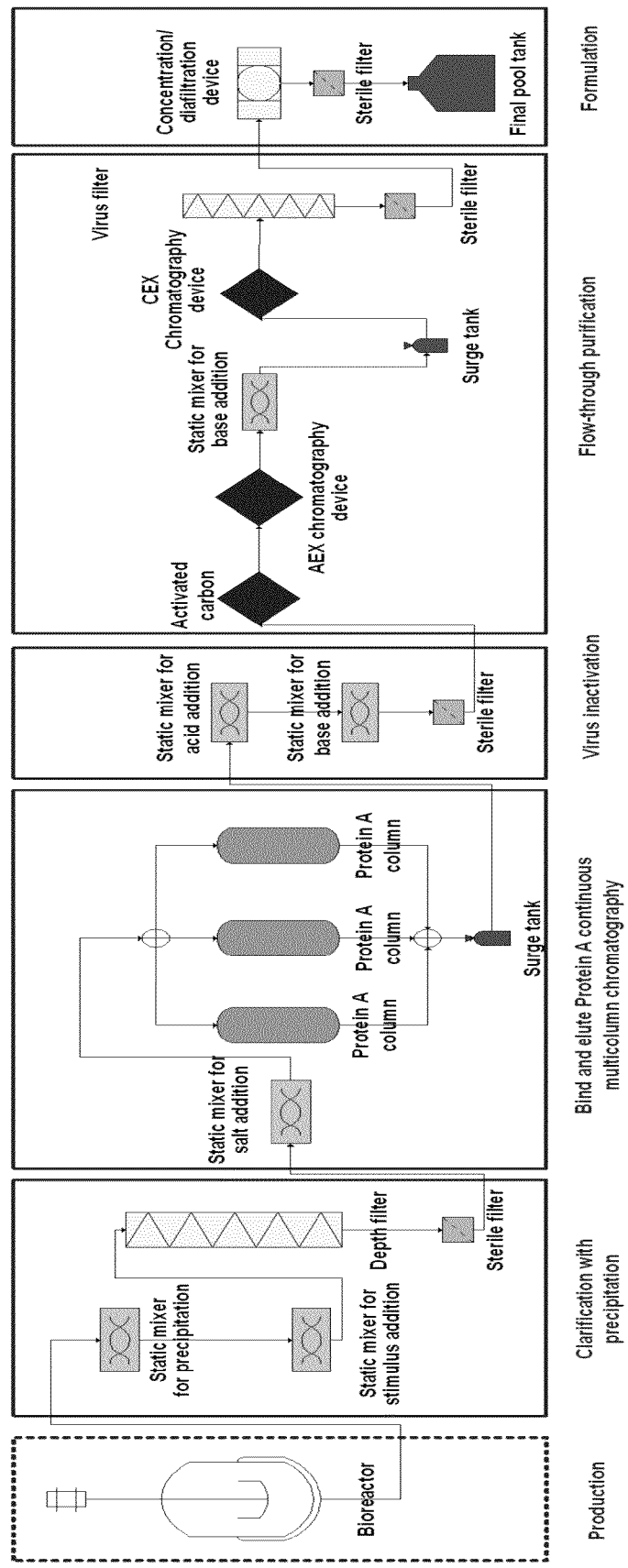
FIG. 15 shows a process for purification of target molecules using the method of the present invention for the bind-and elute chromatography (capture) step. The purification process shown uses a bioreactor for cell culture followed by the following process steps: clarification; Protein A bind and elute chromatography (capture); virus inactivation; flow-through purification; and formulation. As shown, each of the process steps employs one or more devices used to achieve the intended result of the process step. As shown, clarification employs precipitation and depth filtration; Protein A bind and elute chromatography is performed using the process of the present invention; virus inactivation employs two in-line static mixers; flow-through purification employs activated carbon (AC) followed by anion exchange (AEX) chromatography followed by a pH change using an in-line static mixer and a surge tank followed by flow-through cation exchange (CEX) chromatography and virus filtration; and formulation employs a diafiltration/concentration tangential flow filtration device followed by sterile filtration. One or more sterile filters are also employed throughout the process.

As discussed earlier the continuous chromatography concept described above may be used in different chromatography modes (e.g. ion exchange chromatography). Please see FIG. 13 for the potential of this described approach expressed in the scale of binding capacity vs. the residence time. For a single column packed with ESHMUNO® S operation the binding capacity for mAb x decreases with the decreasing residence time due to the mass transfer resistance. For a continuous chromatography approach, the binding capacity does not decrease till certain residence time values showing the potential of higher productivity at shorter residence time values. Additionally the binding capacity values are higher at investigated residence time window. The examples to this case are given below: The monoclonal antibody mAb-y in post-ProtA elution pool solution, which had 5.5 mg/ml monoclonal antibody composing a fraction of 98% of all components in the solution (according to analytical SEC), where HCP amount was 2000 ng/mg antibody (according to immunoenzymetric assay CHO), was purified on the ion exchange resin (ESHMUNO® S) under the following conditions. Chromatography columns: ESHMUNO® S resin was packed in a 16×63 mm column; the column was then equilibrated with 50 mM acetate buffer pH 4.5 at 33 ml/min. In total four columns were packed. To prepare the sample: monoclonal antibody post-ProtA solution was filtered through a 0.45 μm filter. The solution conductivity was at about 2 mS/cm and pH4.8. Accordingly, three or four columns were attached to a continuous chromatographic system, enabling a connection between the first column and the second column, as well as a connection between the second column and the third column and a connection between the third column and the first column or enabling a connection between the first column and the second column, as well as a connection between the second column and the third column and a connection between the third column and the forth column and the connection between the forth column and the first column.

The whole experiment for the three column approach is divided in three steps. As the first step is started first column is connected with the second column. This column group is loaded with the prepared sample at 810 cm/h, while the third column is washed at 1000 cm/h for at least 3 CV with 50 mM acetate pH 4.5, then eluted with 50 mM TRIS buffer, 250 mM NaCl, pH 7.5, following by column cleaning at with 500 mM sodium hydroxyde, following by reequilibration with 50 mM acetate buffer pH4.5.

As the second step is started the second column is connected with the third column. This column group is loaded with the prepared sample at 810 cm/h, while the first column is washed at 1000 cm/h for at least 3 CV with 50 mM acetate pH 4.5, then eluted with 50 mM TRIS buffer, 250 mM NaCl, pH 7.5, following by column cleaning at with 500 mM sodium hydroxyde, following by reequilibration with 50 mM acetate buffer pH4.5.

As the third step is started the third column is connected with the first column. This column group is loaded with the prepared sample at 810 cm/h, while the second column is washed at 1000 cm/h for at least 3 CV with 50 mM acetate pH 4.5, then eluted with 50 mM TRIS buffer, 250 mM NaCl, pH 7.5, following by column cleaning at with 500 mM sodium hydroxyde, following by reequilibration with 50 mM acetate buffer pH4.5. The named steps were repeated at least twice.

Accordingly, the whole experiment for the four column approach is divided in four steps. As the first step is started first column is connected with the second column. This column group is loaded with the prepared sample at 810 cm/h, while the forth column is washed at 810 cm/h for at least 3 CV with 50 mM acetate pH 4.5 and is connected with the third column, then the third column is connected to the second column, and the forth column is washed at 1000 cm/h with 50 mM acetate pH 4.5, then eluted with 50 mM TRIS buffer, 250 mM NaCl, pH 7.5, following by column cleaning at with 500 mM sodium hydroxyde, following by reequilibration with 50 mM acetate buffer pH4.5.

As the second step is started the second column is connected with the third column. This column group is loaded with the prepared sample at 810 cm/h, while the first column is washed at 810 cm/h for at least 3 CV with 50 mM acetate pH 4.5 and is connected with the forth column, then the forth column is connected to the third column, and the first column is washed at 1000 cm/h with 50 mM acetate pH 4.5, then eluted with 50 mM TRIS buffer, 250 mM NaCl, pH 7.5, following by column cleaning at with 500 mM sodium hydroxyde, following by reequilibration with 50 mM acetate buffer pH4.5. As the third step is started the third column is connected with the forth column. This column group is loaded with the prepared sample at 810 cm/h, while the second column is washed at 810 cm/h for at least 3 CV with 50 mM acetate pH 4.5 and is connected with the first column, then the first column is connected to the forth column, and the second column is washed at 1000 cm/h with 50 mM acetate pH 4.5, then eluted with 50 mM TRIS buffer, 250 mM NaCl, pH 7.5, following by column cleaning at with 500 mM sodium hydroxyde, following by reequilibration with 50 mM acetate buffer pH4.5.

As the forth step is started the forth column is connected with the first column. This column group is loaded with the prepared sample at 810 cm/h, while the third column is washed at 810 cm/h for at least 3 CV with 50 mM acetate pH 4.5 and is connected with the second column, then the second column is connected to the first column, and the third column is washed at 1000 cm/h with 50 mM acetate pH 4.5, then eluted with 50 mM TRIS buffer, 250 mM NaCl, pH 7.5, following by column cleaning at with 500 mM sodium hydroxyde, following by reequilibration with 50 mM acetate buffer pH4.5.

The named steps were repeated at least twice.

The eluted fractions resulted in >55 mg/ml packed bed binding capacity and <5% target molecule loss in the loading and ~4% target molecule loss in the elution for the three column concept resulting in 91% product recovery for the three column concept and 96% recovery for the four column concept. The average productivity of 666 g/ml/h for three column concept and of 720 g/ml/h for the four column concept (compared to batch operation the productivity was 76.8 g/ml/h), that composed 99.9% of all components (according to analytical SEC), where HCP amount was in between 400-430 ppm (according to immunoenzymetric assay CHO).

| | RT (min) | Velocity (cm/h) | Recovery (%) | BC (mg/ml) | Productivity (g/L/h) | Purity (ppm) |
|---|---|---|---|---|---|---|
| Batch slow | 3 | 120 | 95 | 45.67 | 76.8 | 425 |
| Batch fast | 0.48 | 810 | 94 | 22.43 | 172.56 | 418 |
| Conti 3 columns | 0.48 | 810 | 91 | 55.5 | 666 | 408 |
| Conti 4 columns | 0.48 | 810 | 96 | 60 | 720 | 433 |

The invention claimed is:
1. A method of purifying target molecules from one or more impurities in a sample, the method comprising the steps of:
   a) providing at least three separation units having the same chromatography matrix which are connected so that liq- uid can at least flow from one separation unit to the subsequent one and from the last to the first separation unit, so that the at least three separation units are connected for a circle of flow between them;

b) feeding the sample to a first separation unit wherein the sample is at a first pH and conductivity enabling the target molecules to be bound to the chromatography matrix in this separation unit, said separation unit is, for at least part of the loading time, in fluid communication with the next separation unit in the circle so that target molecules not bound to the chromatography matrix in said first separation unit bind to the chromatography matrix in the next separation unit, and, at the same time as said feeding steps, at least washing, eluting and re-equilibrating one separation unit different from the separation unit that is being loaded and from the one that is in fluid communication with the separation unit that is being loaded;

c) switching the feed to the next separation unit;

d) feeding the sample on the next separation unit wherein the sample is at a pH and conductivity enabling the target molecules to be bound to the chromatography matrix in said next separation unit, said next separation unit is, for at least part of the loading time, in fluid communication with the separation unit after the next one in the circle so that target molecules not bound to said next separation unit bind to the chromatography matrix in the separation unit after the next, and, at the same time at least washing, eluting and/or re-equilibrating one separation unit different from the separation unit that is being loaded and from the one that is in fluid communication with the separation unit that is being loaded;

e) repeating steps c) and d) one or more times;

wherein the feed is continuous into at least one of the separation units and has a velocity above 800 cm/h and wherein the chromatography matrix of the separation units comprises particles with a diameter between 40 and 200 μm and with pore diameters in the range between 50 nm and 200 nm.

2. The method according to claim 1, wherein the feed has a velocity above 1000 cm/h.

3. The method according to claim 1, wherein three, four or five separation units having the same chromatography matrix are provided in step a).

4. The method according to claim 1, wherein the chromatography matrix of the separation units comprises particles with a diameter between 55 and 100 μm.

5. The method according to claim 1, wherein the chromatography matrix of the separation units comprises particles with pore diameters in the range between 60 nm and 100 nm.

6. The method according to claim 1, wherein in steps b), c) and d), the separation unit that is being loaded is in fluid communication with the next separation unit over the whole loading time.

7. The method according to claim 1, wherein in steps b), c) and d), the fluid communication between the separation unit that is being loaded and the next separation unit starts in the second half of the loading time.

8. The method according to claim 1, wherein the wash liquid eluting during the step of washing the separation unit is directed to the inlet of another separation unit.

9. The method according to claim 1, wherein the sample is a clarified sample.

10. The method according to claim 1, wherein the target molecules that are eluted from the separation units are further subjected to at least one flow through purification step.

11. An apparatus for conducting the method of claim 1, comprising
   at least three separation units having the same chromatography matrix which are connected with connecting lines so that liquid can flow from one separation unit to the subsequent one and from the last to the first separation unit, so that the at least three separation units are connected for a circle of flow between them, and wherein each connecting line between two separation units comprises at least one on/off valve;
   a solvent delivery system that is in fluid connection with the inlet of each separation unit via a branch in the connecting line between the separation units close to the inlet of each separation unit; and
   a fluid outlet line branching from each connecting line between the separation units close to the outlet of a separation unit comprising a line with at least two branches, each branch having an on/off valve.

12. The method of claim 1, wherein the target molecules for purifying are proteins.

13. The method according to claim 12 wherein the process further comprises one or more of the following steps:
   clarification;
   virus inactivation;
   flowthrough purification; or
   sterile filtration.

14. The method according to claim 13, wherein at least two steps of the process overlap in at least a portion of their duration.

* * * * *